US008501402B2

(12) United States Patent
Urthaler et al.

(10) Patent No.: US 8,501,402 B2
(45) Date of Patent: Aug. 6, 2013

(54) METHODS AND DEVICES FOR PRODUCING BIOMOLECULES

(75) Inventors: Jochen Urthaler, Maria Enzersdorf (AT); Roman Necina, Vienna (AT); Christine Ascher, Kundl (AT); Helga Woehrer, Moedling (AT)

(73) Assignee: Boehringer Ingelheim RCV GmbH & Co KG, Vienna (AT)

( * ) Notice: Subject to any disclaimer, the term of this patent is extended or adjusted under 35 U.S.C. 154(b) by 1383 days.

(21) Appl. No.: 10/806,346

(22) Filed: Mar. 23, 2004

(65) Prior Publication Data

US 2005/0026177 A1 Feb. 3, 2005

Related U.S. Application Data

(60) Provisional application No. 60/472,729, filed on May 23, 2003.

(30) Foreign Application Priority Data

Mar. 24, 2003 (EP) ..................................... 03006568

(51) Int. Cl.
*C12Q 1/68* (2006.01)
*G01N 33/00* (2006.01)

(52) U.S. Cl.
USPC ......................................... 435/6.1; 435/69.1

(58) Field of Classification Search
None
See application file for complete search history.

(56) References Cited

U.S. PATENT DOCUMENTS

| | | | |
|---|---|---|---|
| 5,561,064 A * | 10/1996 | Marquet et al. ............ | 435/320.1 |
| 5,637,687 A | 6/1997 | Wiggins | |
| 5,783,686 A * | 7/1998 | Gonzalez ..................... | 536/25.4 |
| 6,268,492 B1 | 7/2001 | Mittelstaedt | |
| 6,274,726 B1 * | 8/2001 | Laugharn et al. ............ | 536/25.4 |
| 6,381,967 B1 * | 5/2002 | Craig ............................. | 62/64 |
| 6,410,274 B1 | 6/2002 | Bhikhabhai | |
| 6,660,472 B1 * | 12/2003 | Santoro et al. ..................... | 435/6 |
| 6,893,879 B2 * | 5/2005 | Petersen et al. ............... | 436/178 |
| 2001/0034435 A1 | 10/2001 | Nochumson et al. | |
| 2002/0012990 A1 | 1/2002 | Lander et al. | |
| 2002/0127704 A1 | 9/2002 | Arakaki et al. | |
| 2006/0106208 A1 * | 5/2006 | Nochumson et al. ........ | 536/25.4 |

FOREIGN PATENT DOCUMENTS

| | | |
|---|---|---|
| EP | 0 376 080 A1 | 7/1990 |
| EP | 0 814 156 A2 | 12/1997 |
| EP | 0 875 271 A2 | 11/1998 |
| WO | WO 90/15148 | 12/1990 |
| WO | WO 93/11218 A1 | 6/1993 |
| WO | WO 95/21250 A2 | 8/1995 |
| WO | WO 9521250 A2 * | 8/1995 |
| WO | WO 96/02658 A1 | 2/1996 |
| WO | WO 96/08500 A1 | 3/1996 |
| WO | WO 96/21729 A1 | 7/1996 |
| WO | WO 96/36706 A1 | 11/1996 |
| WO | WO 97/23601 A1 | 7/1997 |
| WO | WO 97/29190 A1 | 8/1997 |
| WO | WO 98/11208 A1 | 3/1998 |
| WO | WO 99/16869 A1 | 4/1999 |
| WO | WO 99/37750 A1 | 7/1999 |
| WO | WO 99/63076 A1 | 12/1999 |
| WO | WO 00/05358 A1 | 2/2000 |
| WO | WO 00/09680 A1 | 2/2000 |
| WO | WO 01/07599 A1 | 2/2001 |
| WO | WO 02/04027 A1 | 1/2002 |
| WO | WO 02/26966 A2 | 4/2002 |
| WO | WO 02/057446 A2 | 7/2002 |

OTHER PUBLICATIONS

Appendix A:Plasmid purification Protocols, The QIAGEN Transfection Source Book, 1999, pp. 15 and 48-55.*
Definition of Transport, Merriam-Webster OnLine Dictionary, p. 1.*
Definition of connect, Merriam-Webster OnLine Dictionary, pp. 1-2.*
Asenjo, J.A., and Andrews, B.A., "Enzymatic Cell Lysis for Product Release," in *Separation Processes in Biotechnology*, Asenjo, J.A., ed., Marcel Dekker, Inc., New York, NY, pp. 143-175 (1990).
Birnboim, H.C., and Doly, J., "A rapid alkaline extraction procedure for screening recombinant plasmid DNA," *Nucleic Acids Res.* 7:1513-1523, Information Retrieval Limited (1979).
Carlson, A., et al., "Mechanical Disruption of *Escherichia coli* for Plasmid Recovery," *Biotechnol. Bioeng.* 48:303-315, John Wiley & Sons, Inc. (1995).
Ciccolini, L.A..S., et al., "Time Course of SDS-Alkaline Lysis of Recombinant Bacterial Cells for Plasmid Release," *Biotechnol. Bioeng.* 60:768-770, John Wiley & Sons, Inc. (1998).
Ciccolini, L.A.S., et al., "A Mass Balance Study to Assess the Extent of Contaminant Removal Achieved in the Operations for the Primary Recovery of Plasmid DNA from *Escherichia coli* Cells," *Biotechnol. Bioeng.* 77:796-805, John Wiley Sons, Inc. (Mar. 2002).
Chase, H.A., "Purification of proteins by adsorption chromatography in expanded beds," *Trends Biotechnol.* 12:296-303, Elsevier Science Ltd. (1994).
Diogo, M.M., et al., "Separation and Analysis of Plasmid Denatured Forms Using Hydrophobic Interaction Chromatography," *Anal. Biochem.* 275:122-124, Academic Press (1999).

(Continued)

*Primary Examiner* — Maria Marvich
(74) *Attorney, Agent, or Firm* — Michael P. Morris; David L. Kershner; Usha R. Patel

(57) ABSTRACT

A scalable process and device for producing a biomolecule, in particular pharmaceutical grade plasmid DNA. The process includes the steps of alkaline lysis and a neutralization. For separating the lysate and the precipitate, the mixture is allowed to gently flow downward through a clarification reactor that is partially filled, in its lower part, with retention material like glass beads, whereby the precipitate is retained on top of and within the retention. In a preferred embodiment of the lysis step, cell suspension and alkaline lysis solution flow through a lysis reactor that is filled with particulate material like glass beads. The process can be run continuously and fully automated.

31 Claims, 15 Drawing Sheets

OTHER PUBLICATIONS

Figure 1:
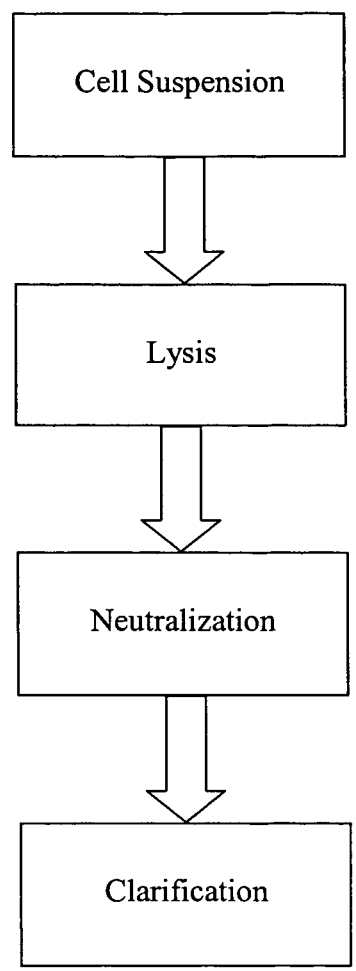

Ferreira, G.N.M., et al., "Development of Process Flow Sheets for the Purification of Supercoiled Plasmids for Gene Therapy Applications," *Biotechnol. Prog. 15*:725-731, American Chemical Society and American Institute of Chemical Engineers (1999).

Ferreira, G.N.M., et al., "Anion exchange purification of plasmid DNA using expanded bed adsorption," *Bioseparation 9*:1-6, Kluwer Academic Publishers (2000).

Foster, D., "Cell Disruption: Breaking Up is Hard to Do," *Biotechnology 10*:1539-1541, Nature Publishing Co. (1992).

Levy, M.S., et al., "Effect of shear on plasmid DNA in solution," *Bioprocess Eng. 20*:7-13, Springer-Verlag (1999).

Levy, M.S., et al., "The effects of material properties and fluid flow intensity on plasmid DNA recovery during cell lysis," *Chem. Eng. Sci. 54*:3171-3178, Elsevier Science Ltd. (1999).

Marquet, M., et al., "Process Development for the Manufacture of Plasmid DNA Vectors for Use in Gene Therapy," *BioPharm. 20*:26-37, UCB-Bioproducts S.A. (1995).

Prazeres, D.M.F., et al., "Large-scale production of pharmaceutical-grade plasmid DNA for gene therapy: problems and bottlenecks," *Trends Biotechnol. 17*:169-174, Elsevier Science (1999).

Rush, M.G., and Warner, R.C., "Alkali Denaturation of Covalently Closed Circular Duplex Deoxyribonucleic Acid," *J. Biol. Chem. 245*:2704-2708, The American Society of Biological Chemists, Inc. (1970).

Theodossiou, I., et al., "The processing of a plasmid-based gene from *E.coli*. Primary recovery by filtration," *Bioprocess Eng. 16*:175-183, Springer-Verlag (1997).

Theodossiou, I., et al., "Methods of enhancing the recovery of plasmid genes from neutralised cell lysate," *Bioprocess Eng. 20*:147-156, Springer-Verlag (1999).

Varley, D.L., et al., "Production of plasmid DNA for human gene therapy using modified alkaline cell lysis and expanded bed anion exchange chromatography," *Bioseparation 8*:209-217, Kluwer Academic Publishers (1999).

Dialog File 351, Derwent World Patents Index, Accession No. 6383967, English language abstract for WO 93/11218 A1 and EP 0 875 271 A2.

Dialog File 351, Derwent World Patents Index, Accession No. 7564643, English language abstract for WO 96/08500 A1.

Dialog File 351, Derwent World Patents Index, Accession No. 8644090, English language abstract for WO 98/11208 A1.

Dialog File 351, Derwent World Patents Index, Accession No. 9536111, English language abstract for WO 99/37750 A1.

Dialog File 351, Derwent World Patents Index, Accession No. 12687730, English language abstract for WO 02/057446 A1.

Ish-Horowicz, D., and Burke, J. F., "Rapid and efficient cosmid cloning," *Nucleic Acids Res. 9*: 2989-2998, IRL Press Unlimited (1981).

Werner, R.G., et al., "pDNA—From Process Science to Commercial Manufacture," *Contract Services Europe* 34-40, Advanstar Communications (2002).

Ferreira G. N. M., et al. "Downstream processing of plasmid DNA for gene therapy and DNA vaccine applications," *Trends in Biotechnology 18*:380-388, Elsevier Publications (2000).

\* cited by examiner

METHODS AND DEVICES FOR PRODUCING BIOMOLECULES

CROSS-REFERENCE TO RELATED APPLICATIONS

The present application claims the priority benefit of U.S. Provisional Application No. 60/472,729, filed May 23, 2003, herein incorporated by reference in its entirety.

BACKGROUND OF THE INVENTION

1. Field of the Invention

The present invention relates to the field of producing biomolecules, in particular polynucleotides like plasmid DNA. In particular, the present invention relates to a method on a manufacturing scale that includes cell lysis under alkaline conditions followed by neutralization and subsequent clarification of the cell lysate.

2. Related Art

The advances in molecular and cell biology in the last quarter of the $20^{th}$ century have led to new technologies for the production of biomolecules (biopolymers). This group of naturally occurring macromolecules includes proteins, nucleic acids and polysaccharides. They are increasingly used in human health care, in the areas of diagnostics, prevention and treatment of diseases.

Recently some of the most revolutionary advances have been made with polynucleotides in the field of diagnostics, gene therapy and nucleic acid vaccines. Common to these applications is the introduction of DNA or RNA into cells with the aim of a diagnostic, therapeutic or prophylactic effect.

Polynucleotides are a heterogeneous group of molecules in terms of size, shape and biological function. Common to all of them are their building blocks (nucleotides as Adenine (A), Guanine (G), Cytosine (C), Thymine (T), Uracil (U)) and their high negative charge under physiological conditions. Representative members of polynucleotides are RNA (messenger RNA, transfer RNA, ribosomal RNA), genomic DNA (gDNA) or chromosomal DNA (cDNA), and plasmid DNA (pDNA). These macromolecules can be single- or double-stranded. Similar to proteins, they are able to build three-dimensional structures and aggregates under distinct conditions. Polynucleotides are sensitive to enzymatic degradation (DNases and RNases) and shear forces, depending on their size and shape. Especially chromosomal DNA, in its denatured and entangled form, is highly sensitive to mechanical stress, resulting in fragments with similar properties to pDNA. This becomes more and more critical with the duration of the shear force exposure (Ciccolini L A S, Shamlou P A, Titchener-Hooker N, Ward J M, Dunnill P (1998) Biotechnol Bioeng 60:768; Ciccolini L A S, Shamlou P A, Titchener-Hooker N (2002) Biotechnol Bioeng 77:796).

Plasmids (pDNA) are double stranded extrachromosomal circular polynucleotides. A typical plasmid contains between 1 and 20 kilo base pairs which corresponds to $3\times10^6$-$13\times10^6$ Da and several thousand Å. Different topological forms of pDNA can be distinguished. The supercoiled (sc) or covalently closed circular (ccc) form is considered as most stable for therapeutic application and is therefore the desired form. The other topological pDNA forms are derived from the ccc form by either single strand nick (open circular or oc) or double strand nick (linear). Breakage of the strands can be caused by physical, chemical or enzymatic activity. For therapeutic use the percentage of ccc form is the main-parameter for assessing the quality of the pDNA preparation.

Therapeutic treatment based on pDNA is considered to be an alternative to treatment with classical chemical drugs or recombinant proteins. Due to the increasing amounts of pDNA required for preclinical and clinical trials, there is a demand for processes that can be performed on a manufacturing scale. These production processes must fulfill regulatory requirements (FDA, EMEA) and should be economically feasible.

In the past, the majority of biotechnological production processes have been developed for manufacturing of purified recombinant proteins. Due to the differences in the physico-chemical properties between polynucleotides and proteins, these methods cannot easily be adapted for the production of polynucleotides. Thus, there is a need for methods that are applicable to polynucleotides, in particular for production of plasmid DNA on a manufacturing scale.

In brief, a process for producing recombinant biomolecules, which are not secreted by the host, in particular DNA and large proteins, follows the steps of:

a) Fermentation (cultivation of cells that carry the biomolecule of interest and optionally harvesting the cells from the fermentation broth), b) Disintegration of the cells (release of the biomolecule of interest from the cells), c) Isolation and purification (separation of the biomolecule of interest from impurities).

These steps are more specifically characterized for the production of polynucleotides, in particular for the production of pDNA, as follows:

Currently, *E. coli* is the most commonly used host for pDNA production. Other bacterial, yeasts, mammalian and insect cells may also be used as host cells in the fermentation step. Selection of a suitable host strain is of major importance for the pDNA quality. A high cell density and plasmid copy number and its stable maintenance during the fermentation are crucial for a robust economic process. For this purpose, a well-defined culture medium is needed. The end point of fermentation and the conditions during cell harvest, which usually follows fermentation, contribute to the quality of the polynucleotide (Werner R G, Urthaler J, Kollmann F, Huber H, Necina R, Konopitzky K (2002) Contract Services Europe, a supplement to Pharm. Technol. Eur. p. 34).

After fermentation, the cells are usually harvested, mostly by means of centrifugation. The harvested wet biomass is resuspended in an appropriate buffer. Before final isolation (by e.g. column chromatography, ultradiafiltration, extraction or precipitation) of the polynucleotide of interest from proteins, gDNA, RNA and other host related impurities, the cells need to be processed, either directly or after freezing and thawing. Alternatively to harvesting and resuspending the cells before further processing, the fermentation broth per se may be subject to further processing (WO 97/29190).

Processing starts with disintegration of the cells and ends with the first isolation step of the polynucleotide of interest, which is also termed "capture step".

Disintegration of the cells can be achieved by physical, chemical or enzymatic methods. Most of currently available procedures were developed for the release of proteins from the cells and can not be used for polynucleotides without certain adaptations. Limitations of the established techniques are due to the differences of the physico-chemical properties between proteins and polynucleotides. High-pressure homogenization, the most common technology for the recovery of proteins, cannot be used for polynucleotides due to their size-depending shear force sensitivity and possible destruction of gDNA. (Carlson A, Signs M, Liermann L, et al. (1995) Biotechnol Bioeng 48:303). Chemical (Foster D (1992) Biotechn 10, (12):1539) and enzymatic (Asenjo J A, Andrews B A (1990) Bioprocess Technol 9: 143) methods cause minimal mechanical stress and minimal irreversible deterioration of the plasmid. Since it is the gentlest method, enzymatic disintegration utilizing lysozyme is the method of choice on laboratory scale. Typically, lysozyme is animal-derived (most commonly from chicken egg white) and therefore its use is a potential health risk (prions) and is considered as problematic by regulatory authorities like FDA or EMEA. Using recombinant lysozyme involves high raw material costs and analytical efforts. Thermal treatment of the cells is another option for a disintegration technique that avoids shear forces, as described in WO 02/057446 A2 and WO 96/36706. The suspension of microorganisms processed by short time exposure (30 seconds to some minutes) to 80° C. in a sink heater or in a filter (with filtering aids). This method is usually carried out in combination with a detergent (e.g. TRITON®) and lysozyme.

Usually, disintegration and release of plasmid DNA from bacterial cells is performed by alkaline lysis (a chemical method) as described by Birnboim and Doly (Birnboim H C, Doly J (1979) Nucl Acids Res 7: 1513).

The disintegration/release process disclosed therein can be divided into two steps, the first one being the intrinsic cell disintegration or lysis step and the second one being the neutralization step.

During alkaline lysis, cells are subjected to an alkaline solution (preferably NaOH) in combination with a detergent (preferably SDS). In this environment, the cell wall structures are destroyed thereby releasing the polynucleotide of interest and other cell related compounds. Finally, the solution is neutralized by addition of a solution of an acidic salt, preferably an acetate, in particular potassium acetate (KAc) or sodium acetate (NaAc). The alkaline conditions lead to denaturation of pDNA by unwinding the supercoiled structure. Up to a pH-value of 12 to 12.5 the complete separation of the complementary strands is prevented. This enables entire renaturation of the plasmid molecule, when the pH is decreased again. If the pH-value exceeds the renaturation limit, the unseparated regions are lost and the pDNA is irreversibly denatured. At this stage the polynucleotide contains large domains of single stranded material (with a large exposure of hydrophobic bases) (Diogo M M, Queiroz J A, Monteiro G A, Prazeres D M F (1999) Analytical Biochemistry 275:122). The exact pH-value for irreversible denaturation of the plasmid is strongly influenced by the base pair composition, the resulting hydrogen bonds and its size (WO 97/29190). In parallel, genomic DNA and proteins are denatured, too. Denaturation of DNA leads to entanglement and formation of long single pair strands with low mechanical stability. Impact of mechanical stress may cause breakage of DNA, especially of the large gDNA molecules. The resulting fragments have properties comparable to those of pDNA. Since precipitation during the subsequent neutralization step is a size dependent process, these fragments may remain soluble and thus behave similarly to pDNA (Marquet M, Horn N A, Meek J A (1995) BioPharm September:26). Therefore they would interfere during the isolation process. The incubation time at high pH value is critical for the renaturation of the target polynucleotide, the degree of cell disintegration and the genomic DNA content in the preparation. Therefore the main parameter for quality and quantity of the polynucleotide preparation is the contact time with the alkaline lysis solution. Usually RNAse is added to the suspension to digest RNA into small pieces not to interfere the isolation process (Sambrook J, Fritsch E F, Maniatis T, (1989) Molecular Cloning: A Laboratory Handbook, CSH Press, Cold Spring Harbor, USA). After addition of NaOH and SDS, the solution becomes highly viscous. Local pH extremes, which irreversibly denature the plasmid (Rush M G, Warner R C (1970) J Biol Chem 245:2704) have to be avoided. Fast and efficient mixing has to be guaranteed in order to achieve a homogenous solution. Usually small containers like glass bottles containing the viscous solution are mixed very gently by hand (QIAGEN® Plasmid-Handbuch January 2001, Qiagen GmbH, Germany). This procedure can only be performed in a batchwise mode with a maximum of about 5 l lysate per bottle. It is mainly operator dependent, providing low reproducibility and is therefore not suited for a manufacturing scale. For large scale conventional stirrers are not suited because they may cause damage to pDNA and gDNA. Some processes use optimized tanks and stirrers or a combination of different mixers in order to overcome these problems (Prazeres D M F, Ferreira G N M, Monteiro G A, Cooney C L, Cabral JMS (1999) Trends Biotechnol 17:169; WO 02/26966).

In the subsequent neutralization step, cell debris, proteins as well as genomic DNA are co-precipitated with SDS by formation of a complex floccose precipitate (Levy M S, Collins I J, Yim S S, et al. (1999) Bioprocess Eng 20:7). Again gentle, but homogeneous blending (homogeneous neutralization) is essential for complete precipitation and for maintenance of pDNA quality. Vigorous mixing causes destruction of the plasmid and the flocks, resulting in redissolution of the impurities precipitated before (Levy M S, Ciccolini L A S, Yim S S, et al. (1999) Chem Eng Sci 54:3171; Marquet M, Horn N A, Meek J A (1995) BioPharm (September):26). This burdens the subsequent chromatographic separations (by e.g. loss of capacity for pDNA or the negative impact on the separation of RNA and gDNA, which have similar binding properties).

In the next step that follows alkaline lysis and neutralization, the precipitate has to be separated from the plasmid containing solution (this step is, in the meaning of the present invention, termed "clarification step"). In view of further purification by means of a resin, it is often necessary to adjust the parameters of the solution (like salt composition, conductivity, pH-value) to guarantee binding of the desired polynucleotide on the resin (this step is, in the meaning of the present invention, termed "conditioning step"). Subsequently, the solution is subjected to the first chromatographic step (capture step).

Centrifugation on fixed angle rotors (is the most frequently used method employed as the clarification step on laboratory and pre-preparative scales (Ferreira G N M, Cabral J M S, Prazeres D M F (1999) Biotechnol Prog 15:725). For lysate amounts usually handled in bottles the clear liquid phase separating from floating flocks and descending precipitate is sucked off and filtered. Otherwise the big flock-volume would shortly block the used filter. Since the fluid between the flocks contains residual plasmid DNA (Theodossiou I, Collins I C, Ward J M, Thomas O R T, Dunnhill P (1997) Bioprocess Engineering 16:175), high losses have to be taken into account. As further problem strong adsorption of nucleotides and pDNA to many filter-media has to be mentioned (Theodossiou I, Collins I J, Ward J M, Thomas O R T, Dunnhill P (1997) Bioprocess Eng 16:175; Theodossiou I, Thomas O R T, Dunnhill P (1999) Bioprocess Eng 20: 147). In many cases, bulk filter materials or bag filters are used for clarification of the lysate. Since these materials are either not certified or not scalable, they are not applicable for the production of pharmaceutical-grade plasmids on a manufacturing scale. More recent technologies utilize expanded bed adsorption (EBA), which allows removal of precipitated material while capturing the desired product (Chase H A (1994) Trends Biotechnol 12: 296). For capturing plasmid DNA direct after lysis by this chromatographic technique, it has to be taken into account that due to the large diameter of the (during neutralization built) aggregates of flocks pre-clarification prior to EBA is essential (Ferreira G N M, Cabral J M S, Prazeres D M F (2000) Bioseparation 9:1; Varley D L, Hitchcock A G, Weiss A M E, et al. (1998) Bioseparation 8:209).

There have been several attempts to develop improved technologies for each of the above-described steps. These attempts were mostly based on the following considerations:

Resuspension of the cells has to be carried out as fast as possible (especially when the cells have been frozen before), while avoiding high shear forces. Several commercially available types of stirrers are available for mixing the cell paste with the resuspension buffer in a batchwise mode in a vessel until homogeneity is achieved, the most commonly used device being a magnetic or impeller stirrer. Another method is described in US 2001 0034435 A1. Here the cell paste is diluted with a resuspension buffer and the cell/buffer mixture is circulated through a static mixer in a pump-around mode. It has also been suggested to directly dilute the fermentation broth with the resuspension buffer in a static mixer prior to lysis (WO 97/23601 A1).

For disintegration (lysis) of the cells in view of obtaining polynucleotides, several different methods have been suggested, e.g. methods that use thermal or chemical treatment. For the thermal lysis, a process using a flow-through heat exchanger (70-100° C.), in which the cells are continuously disintegrated after incubation of the resuspended cells in presence of a detergent and optionally lysozyme, is described (WO 96/02658 A1). Another physical method, which works in a temperature range of 70-90° C., is shown in WO 02/057446 A2: In a first step, the harvested cells are filtered utilizing filter aids and the resulting mixture is thermally lysed in a second step. Alternatively, disintegration can be carried out by pumping hot lysis buffer through the filter cake or by a flow through heat exchanger. Chemical lysis methods are operated at an alkaline pH-value, they are therefore referred to as "alkaline lysis". A commonly used composition of the intrinsic lysis solution is described by Birnboim and Doly, but there are exist many variants of this solution. As the detergent that is part of lysis solution usually SDS is used, but other (e.g. non-ionic) detergents like TWEEN® or TRITON® are also suitable (e.g. WO 95/21250 A2). According to EP 0376080 A1, SDS is replaced by desoxycholate (DOC), while the three phase extraction method of U.S. Pat. No. 5,637,687 uses a novel composition for the cell-solubilization (benzyl alcohol+sodium iodide+guanidinium thiocyanate and/or guanidinium chloride). Most methods for alkaline lysis are operated in a batchwise mode. By way of example, the alkaline treatment can be carried out directly by adding a NaOH/SDS solution to a bacterial cell culture during exponential growth (in this case, no harvest of the cells is performed) or after resuspension of the cells in a proper buffer. Thereby, an alkaline solution is added until a pH value is reached that is 0.2 units lower than the pH value at which the pDNA-molecules are completely denatured, a pH value that is empirically determined and different for each single plasmid (WO 97/29190 A1). Another method utilizes a column comprising a carrier on a membrane filter that is capable of retaining a solution and permeating it by aspiration. When adsorbed onto the carrier, a certain amount of cells can be lysed in this column by means of lysozyme and further processed (EP 0814156 A2). A similar device that consists of a hollow body (tube) with a built-in filtration-layer is disclosed in EP 0616638 B1, EP 0875271 A2, and WO 93/11218 A1. Alkaline lysis is carried out in the part of the tube above the filtration section. The cell suspension and the used solutions are distributed and mixed in a non-continuous way.

The above-described methods are operated in non-continuous open systems that bear the risk of possible contamination. Handling and mixing is not automated and therefore user-dependent. The only way to handle larger pDNA-amounts, is multiplication of the devices, e.g. running them in parallel. These methods and devices are not suitable for production of pharmaceutical grade polynucleotides on a manufacturing scale. To achieve contacting and mixing of the cells with the lysis solution, it has also be suggested to use static mixers or simple tubings. This approach has been described for a cell lysis method, which is based on simply connecting the streams containing the pumped cell suspension and the lysing agent at a defined meeting point. The contact time is defined by the tubing volume (diameter and length of the tube) behind the meeting point and by the pump-velocity of the connected streams through the tubing. To facilitate rapid homogenization, the inner diameter of the tubing has to be reduced (2-8 mm) (WO 99/37750 A1). For connecting the two pumped streams at the meeting point, "Y"-connectors are proposed (WO 00/09680 A1). To enhance homogenous mixing of the cells with the lysis solution, especially designed static mixers are suggested. These devices are commercially available continuous flow-through supports. The contact time of the cells with the lysis solution is defined by the mixer dimensions and the flux (WO 97/23601 A1, WO 00/05358 A1). These online-contacting devices can also be combined with a subsequent stirred tank reactor. In this stirred tank reactor the neutralization step may also take place. (WO 02/26966 A2). Another process describes the combination of a static mixer, a so called "lysis coil" and an impeller (US 2001/0034435 A1).

The above-described continuous methods either work with simple connections of the flow stream or, in the case of using static mixers, with various fixtures, (e.g. helical structures).

Among the above-described methods, those using a simple tubing do not guarantee homogenous mixing, while the variant with the reduced tubing diameter (<1 cm) was designed for small-scale applications. The methods using static mixers (or reduced tubing diameters) may cause high shear forces to the polynucleotides.

In the neutralization step, normally an acidic solution containing potassium acetate is used. For concurrent precipitation of RNA, compositions that contain, in addition, sodium chloride, potassium chloride or ammonium acetate (up to 7 M) have been suggested (US 2001/0034435 A1). It was also shown that a solution containing divalent alkaline earth metal ions like $CaCl_2$ that is added to the mixture after neutralization results in the precipitation of RNA and chromosomal DNA (U.S. Pat. No. 6,410,274 B1).

Neutralization of the lysed cell solution is often carried out as one single step in a batch mode. In EP 0814156 A2, WO 93/11218 A1, EP 0616638 B1, and EP 0875271 A2 the lysed cell solution is contacted with the neutralization/precipitation solution in the same device (column or tube with an in-line filter-material) like used before for the lysis step (already described above). Again, these techniques would be subject to several major limitations when transferred to the manufacturing scale production of pharmaceutical-grade polynucleotides, the problems also being possible contamination due to the non-continuous open system, user-dependence, and lacking scalability.

For the neutralization step, a stirred tank reactor that already contains the lysed cell solution, has been suggested, into which the neutralization solution is filled under continuous mixing with the stirrer at a speed of 500 rpm (WO 02/26966). A similar method is claimed in US 2001/0034435 A1, according to which neutralization is achieved by mixing the solutions with an impeller in a chilled jacketed holding tank or before in an in-line static mixer. Two very simple continuous contacting techniques are disclosed in WO 99/37750 A1 and WO 00/09680 A1. Both methods use the same setup as already described above for the lysis step connecting the two pumped streams at a meeting point with a reduced inner diameter of the resulting tubing (WO 99/37750) or a simple "Y" connector and tubing (WO 00/09680). For both methods, static mixers may be used in the neutralization step (WO 97/23601 A1, WO 00/05358 A1). These mixers are utilized in the same manner already described above for the lysis step.

The contact time of the pDNA-with the lysis solution has a major impact on its quality and depends on the time point and effectiveness of the neutralization step. Therefore, mixing of the lysed cell solution with the neutralization solution has to be fast and homogenous. This requirement can not be met by the techniques utilizing stirred tank reactors. Fast mixing with an impeller may cause rupture of the precipitated flocks and re-dissolution of impurities. The methods using a simple tubing do not guarantee homogenous mixing, while the variant with the reduced tubing diameter (<1 cm) may also cause undesired destruction of the flocks and is not suitable for larger scales. Although static mixers are expected to achieve homogenous mixing, they may get blocked due to the large volume of the flocks. Another disadvantage is that genomic DNA may be sheared by the internal structure of the mixer to a size, which will cause problems in the subsequent purification steps, let alone the possible negative impact of the mechanical stress to the desired polynucleotide.

To obtain a cleared lysate; the precipitated material has to be separated from the polynucleotide containing solution. Conventionally this clarification step is carried out in a batchwise mode using techniques known in the art like filtration or centrifugation (e.g. US 2001/0034435 A1, WO 02/04027 A1). Most commonly, the filters are depth filters (WO 00/09680). Other filter means for macrofiltration are macroporous diaphragms consisting of e.g. compressed gauze or an equivalent filter material (EP 0376080 A1). According to some protocols, filtration is carried out in presence of a filter aid (WO 95/21250 A2, WO 02/057446 A2, US 2002/0012990 A1). WO 96/21729 A1 discloses a method that contains a filtration step using diatomaceous earth after a centrifugation step, thereby achieving the additional effect of reducing the RNA content. Furthermore, combinations of a membrane filter with a loose matrix (glass, silica-gel, anion exchange resin or diatomaceous earth), which concurrently act as carrier for DNA, have been described (EP0814156A2). According to WO 96/08500 A1, WO93/11218 A1, EP 0616638 B1 and EP 0875271 A2, clarification is achieved by a device that has been described above for the lysis and for the neutralization step, whose filtration part may consist of different materials (e.g. glass, silica-gel, aluminum oxide . . . ) in the form of loose particles, layers or filter plates (especially with an asymmetric pore size distribution). The flux through the filter is accomplished by gravitation, vacuum, pressure or centrifugation. As a continuous clarification method, centrifugation (e.g. disc stack centrifuge or decanting centrifuge) are mentioned (WO 99/37750 A1, WO 96/02658 A1). Also combinations of centrifugation followed by filtration are described for the clarification purpose (WO 02/26966 A2, WO 96/02658 A1).

The above-described clarification methods are usually carried after the material has been incubated with the neutralization buffer for a certain period of time. This does not allow continuous connection with the foregoing steps and is only suitable for the laboratory scale. Apart from this, filtration techniques are usually carried out in open devices with the risk of possible contamination. Since any material that is used in a cGMP process must be validated, additional filter aids that might improve performance of the filtering process, are usually avoided.

In general, conventional filters have a limited capacity and are soon blocked by the large amount of voluminous flocks. In addition, a constant flux over the precipitate that is retained by the material may result in destruction of the flocks and re-dissolution of impurities, which would again have a negative impact on the following steps. For larger amounts of pDNA it has been suggested for some devices to multiply them (e.g. run them in parallel), which is insufficient for operating on a manufacturing scale. Centrifugation could be applicable continuously, but due to the sensitivity of polynucleotides to shear forces this treatment may also cause degradation of plasmid DNA and genomic DNA and detachment of precipitated impurities by rupture of the flocks.

In the subsequent conditioning step, the salt composition and/or the conductivity and/or the pH-value of the cleared lysate is adjusted to a value (to be determined empirically) that ensures binding to the resin in the subsequent capture step. Several conditioning methods have been described, e.g. in WO 97/29190 A1, WO 02/04027 A1 and WO 98/11208 A1. In the methods described in EP0814156A2, WO93/11218 A1, EP 0616638 B1 and EP 0875271 A2 the conditioning step is carried out as a washing and eluting step in the same device in which the previous steps took place.

Furthermore, as a pretreatment before the final purification, addition of an "Endotoxin Removal (ER) Buffer" (QIAGEN®) (WO 00/09680 A1) or TRITON X®-114 (WO 99/63076 A1) has been suggested.

Common to all of the described methods is their non-continuous and non-automated mode of operation that does not connect the operational steps.

For capturing the polynucleotide of interest, several techniques are known in the art, e.g. tangential flow filtration (WO 01/07599 A1), size exclusion chromatography (WO 96/21729 A1, WO 98/11208), anion exchange chromatography (WO 00/09680 A1, U.S. Pat. No. 6,410,274 B1, WO 99/16869), hydrophobic interaction chromatography (WO 02/04027 A1).

It has already been suggested combining some of the steps described above, e.g. for the processes described in EP 0814156 A2, WO 93/11218 A1, EP 0616638 B1 and EP 0875271, according to which cell lysis, neutralization, clarification, washing, optionally conditioning and capturing are carried out in the same apparatus. Typically, these methods are open systems that are operated in a non-automated/non-continuous mode including several holding steps. The devices are only suitable for the laboratory scale and cannot be transferred into manufacturing scale. The techniques also lack of reproducibility and suitability for cGMP large-scale production.

Alternatively, combinations utilizing different devices have been described, in which the individual steps are directly connected with each other.

The continuous combination of two ore more steps has been described in several patent documents: WO 96/02658 A1 describes the combination of thermal lysis and clarification by means of a centrifuge, WO 00/09680 A1 and WO 02/26966 A2 suggest combining alkaline lysis and neutralization. The methods described in US 2001/0034435 A1 and WO 97/23601 A1 combine the three steps resuspension of the cells, alkaline lysis and neutralization; WO 00/05358 A1 and WO 99/37750 A1 describe the combination of alkaline lysis, neutralization and clarification by centrifugation.

None of these processes combines more than three steps of the isolation procedure, the first step being the resuspension step and last one being the capture step. The devices used in these methods for contacting the solutions during lysis and neutralization do either not guarantee homogenous mixing or may apply disadvantageous shear forces to the solutes.

SUMMARY OF THE INVENTION

It was an object of the invention to provide a method for isolating a biomolecule, in particular a polynucleotide, of interest from a cell culture that overcomes the limitations of the known methods. Such method should be suitable for the production of therapeutically applicable polynucleotides. Thus, such process should neither require the use of enzymes like RNase and lysozyme nor the use of detergents apart from SDS.

In particular, it was an object of the invention to provide a automatable and scalable process for isolating a polynucleotide of interest, in particular plasmid DNA, on a manufacturing scale that includes, as a cell disintegration step, an improved alkaline lysis method. In addition to an alkaline lysis step, the process should include a neutralization step, a clarification step, and optionally a conditioning step and/or a concentration step.

To solve the problem underlying the invention, the following steps were taken:

Since clarification of the lysate was considered to be the limiting step for operating a process for isolating a biomolecule of interest in a continuous and automated way, in a series of experiments, several different methods were investigated to address the issue of clarification. It was surprisingly found that a tank that is filled with glass beads to a certain level and has an outlet at the bottom, provides excellent clarification results and allows automation of the entire process.

Furthermore, it was sought to provide an improved method for achieving disintegration of the bacterial cells by alkaline lysis that may be combined with the improved clarification step. To this end, several mixing techniques were tested in preliminary experiments using differently colored test solutions. It was surprisingly found that a tube filled with glass beads leads to sufficient mixing and contacting of two solutions when brought together by pumping through this tube. This finding was confirmed when using, as the two solutions, the resuspended cell suspension and the lysis solution.

A further unexpected result was obtained when procedures for mixing the lysed cell solution with the neutralization solution were tested. It was found that after connecting the streams of the pumped lysed cell solution with the stream of the pumped neutralization solution by a conventional T-connector, an especially oriented tubing results in satisfactory mixing of the solutions and formation of compact voluminous flocks, which are not influenced by strong shear forces.

These findings were developed further by combining the single steps to a system that can be operated in a continuous mode and automated.

The present invention relates to a process for producing a biomolecule that is not secreted by the host cell, comprising the steps of
a) cultivating cells to produce the biomolecule of interest and optionally harvesting and resuspending the cells,
b) disintegrating the cells by alkaline lysis,
c) precipitating the cell debris and impurities by neutralizing the lysate,
d) separating the lysate from the precipitate obtained in step c),
e) purifying the biomolecule of interest,
wherein in step d) the mixture comprising the precipitate and the lysate is allowed to gently flow downward through a clarification reactor that is partially filled in its lower part with retention material, whereby the precipitate is retained on top of and within the layer of retention material and the cleared lysate leaves the reactor through an outlet in the bottom of the reactor.

BRIEF DESCRIPTION OF THE DRAWINGS/FIGURES

Figure 2:
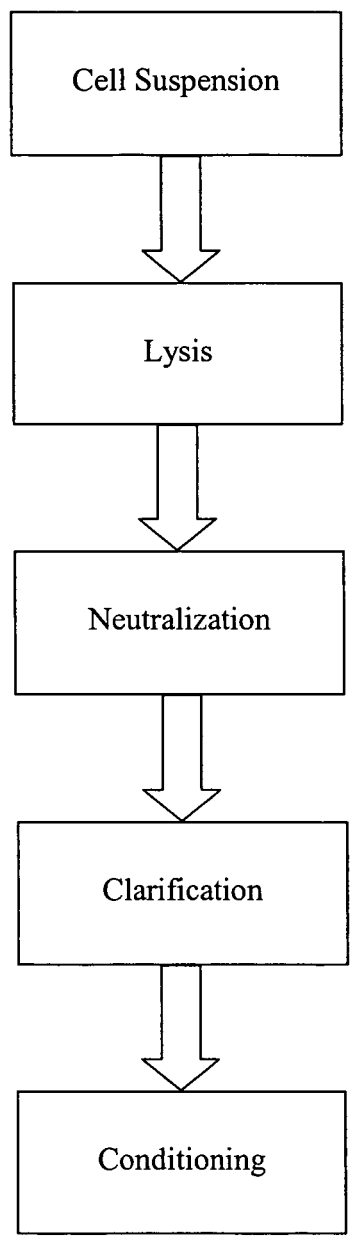
Figure 3:
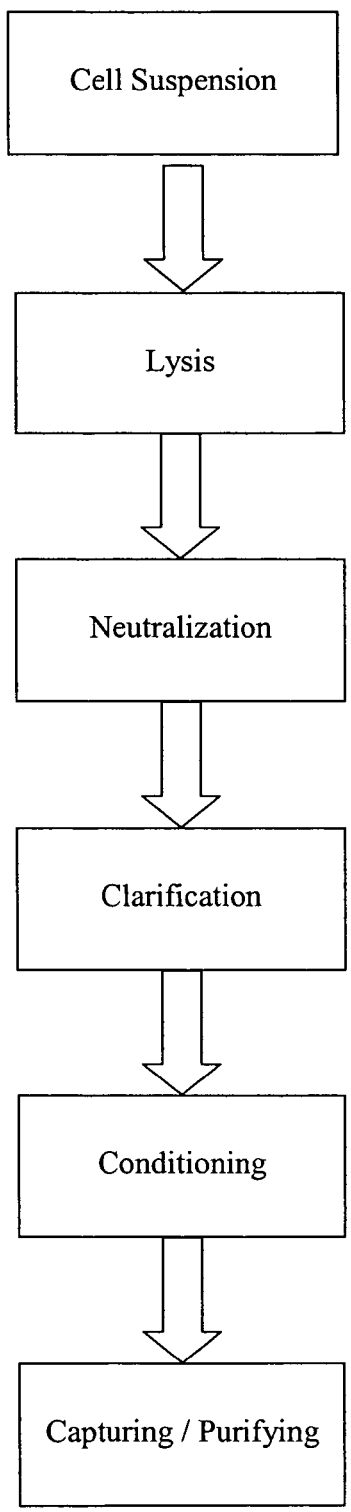
Figure 4:
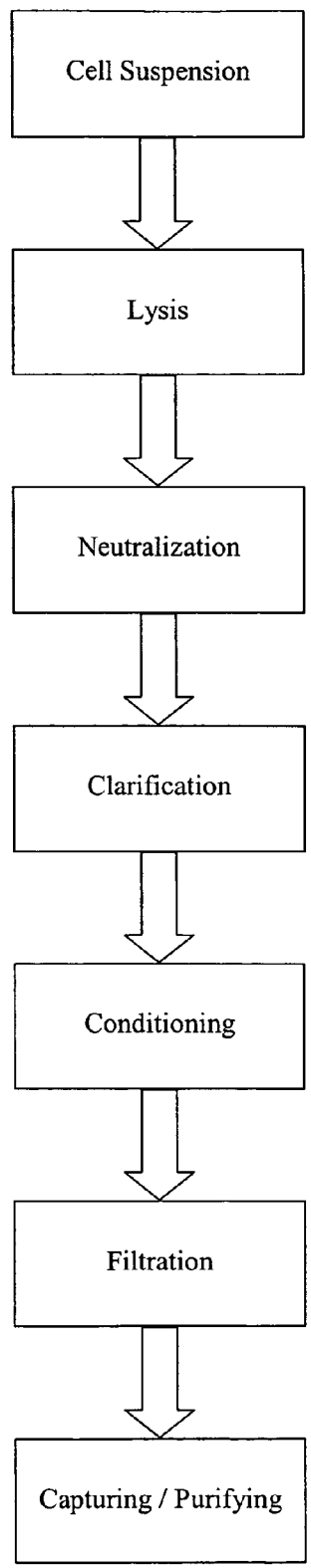
Figure 5:
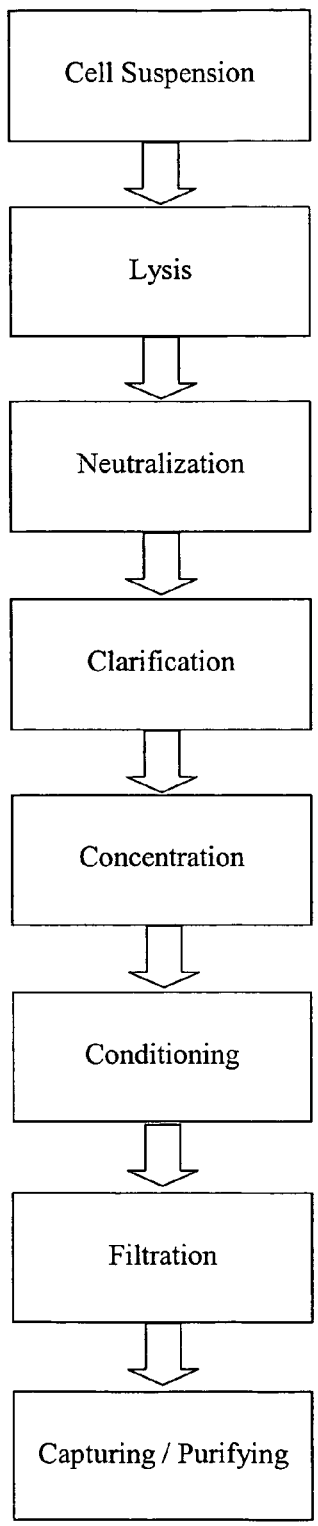

FIG. 1: Flowchart of a combined continuous three step process comprising alkaline lysis, neutralization and clarification FIG. 2: Flowchart of the combined continuous three-step process of FIG. 1, extended by a continuous conditioning step FIG. 3: Flowchart including an additional capture step FIG. 4: Flowchart of the combined continuous system including an on-line filtration step between conditioning and capture step FIG. 5: Flowchart of the combined continuous process (FIG. 4) extended by a concentration step before conditioning FIG. 6: Scheme for the continuous combination of alkaline lysis, the neutralization and the clarification reactor FIG. 7: Device comprising a combination of lysis reactor, neutralization reactor and clarification reactor (pilot apparatus suitable for up to 1 kg wet cells)

Figure 7:
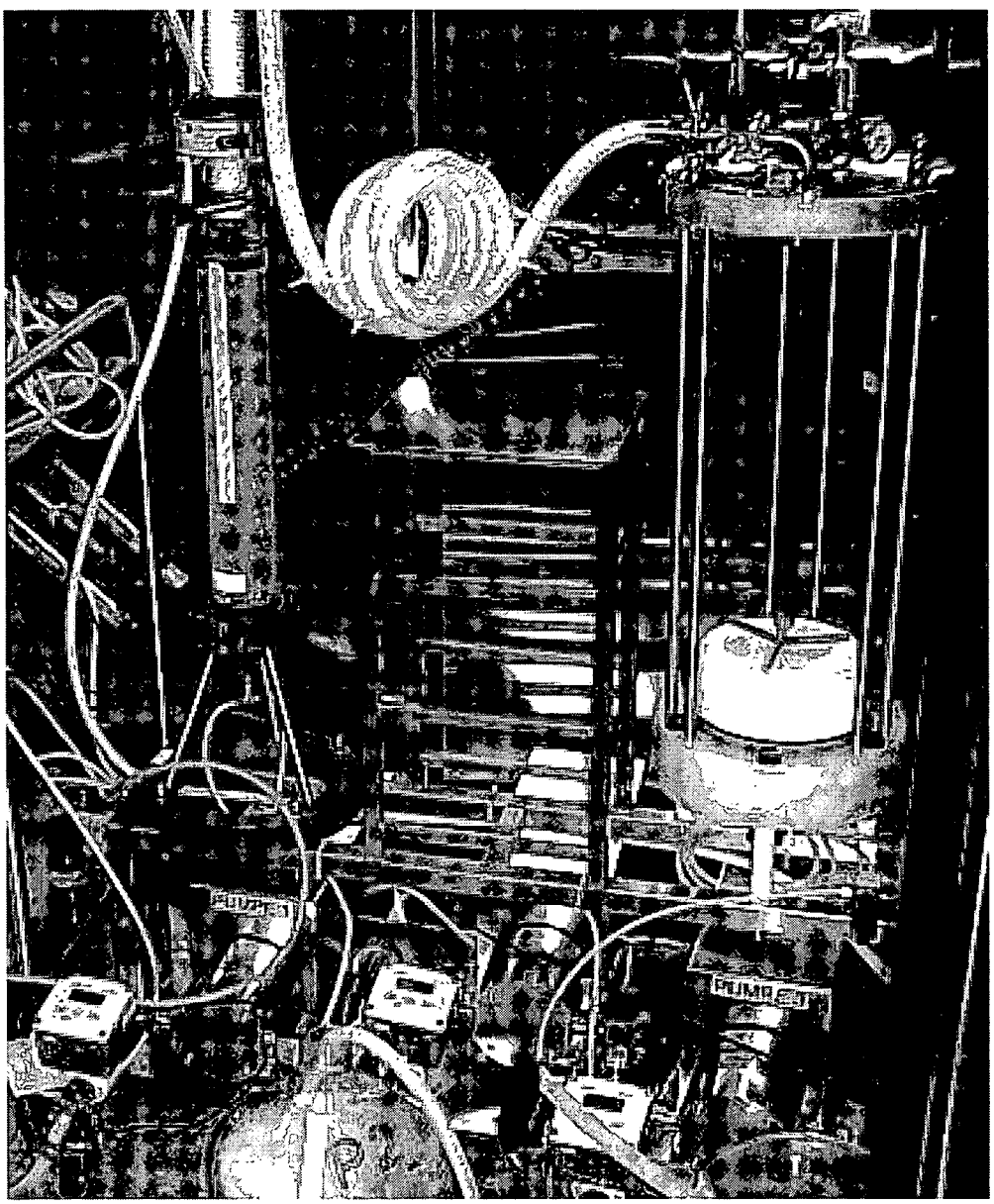
Figure 8:
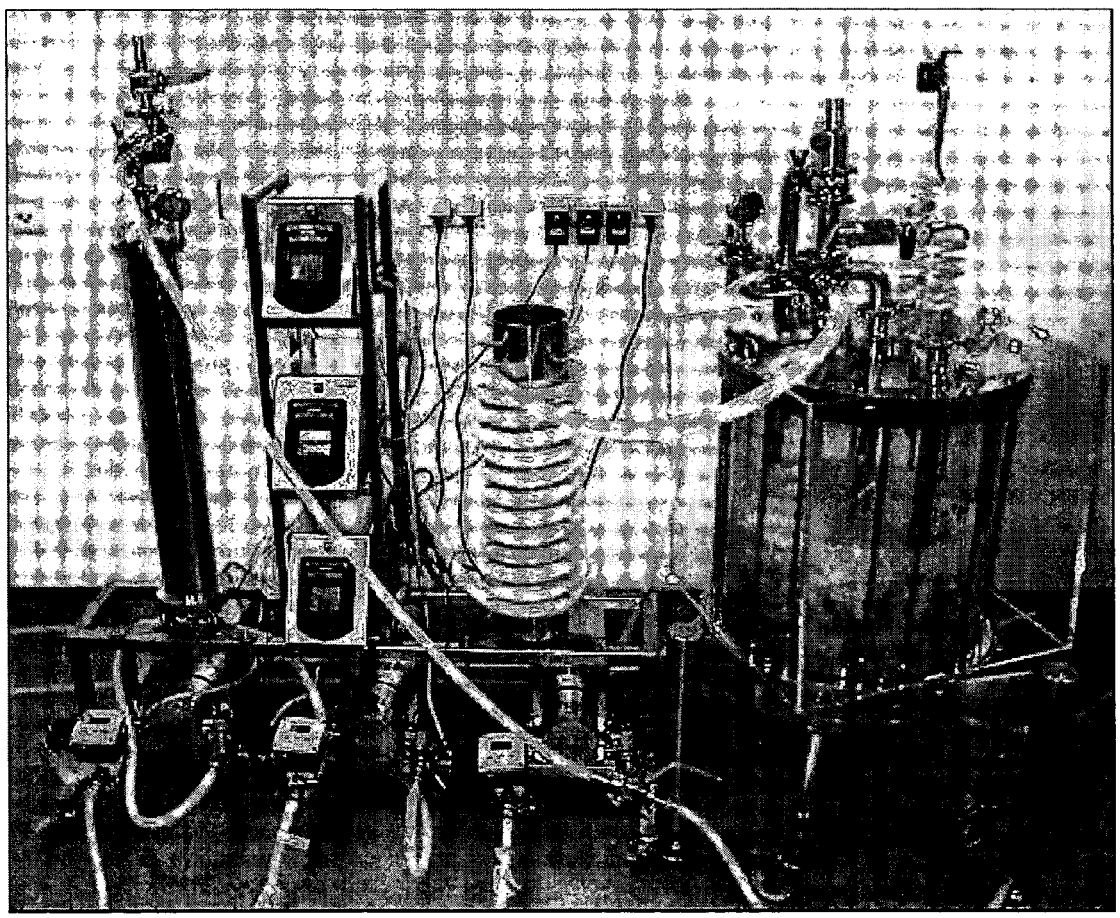

FIG. 8: Up-scaled version of the device of FIG. 7 (pilot apparatus suitable for up to 6 kg wet cells)

Figure 9:
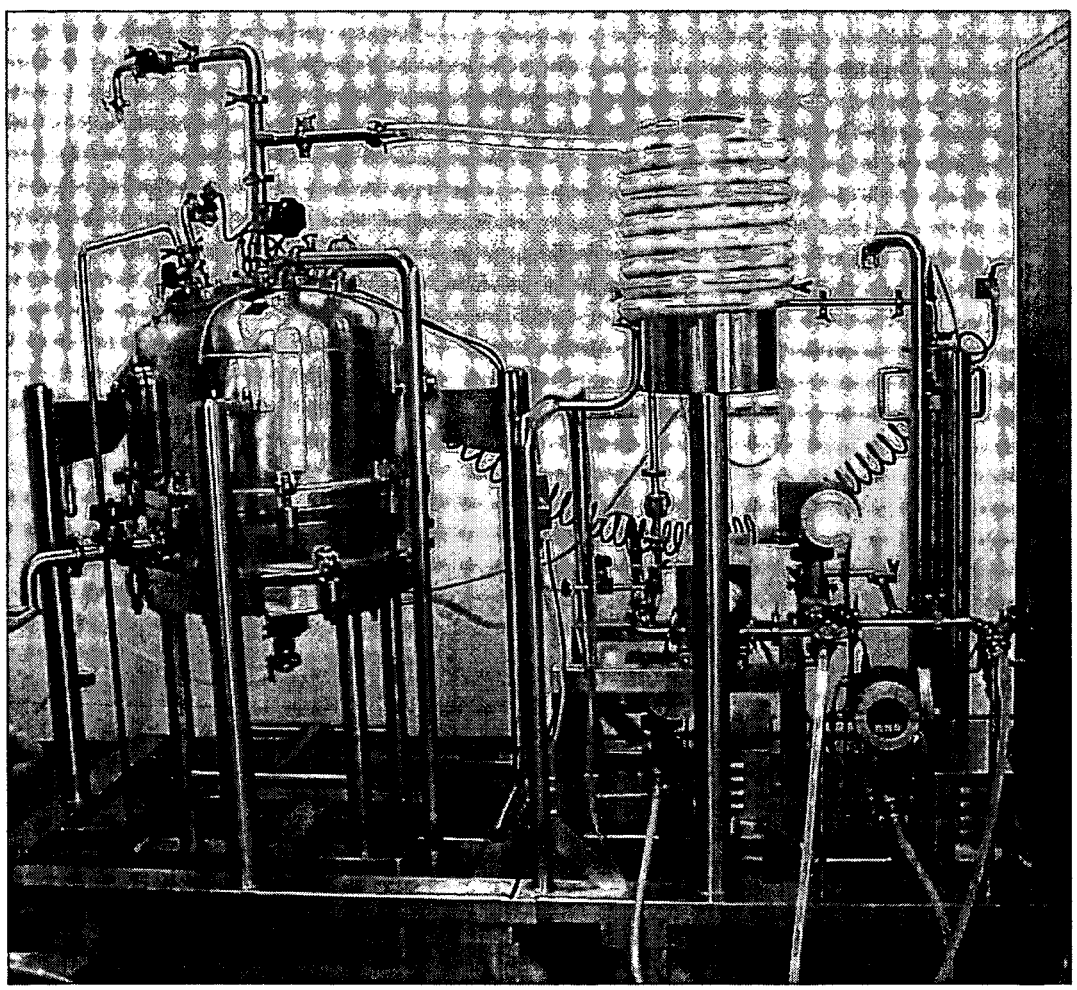

FIG. 9: cGMP device comprising a combination of lysis reactor, neutralization reactor and clarification reactor (suitable for up to 20 kg wet cells)

Figure 10:
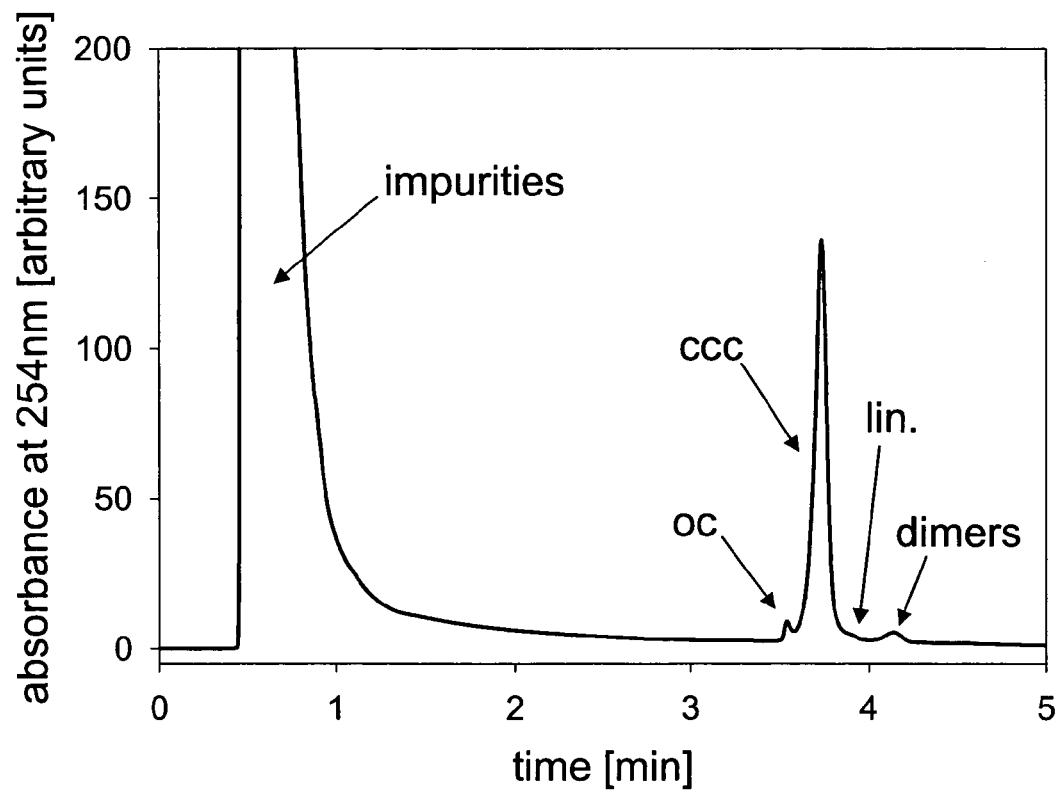
Figure 11:
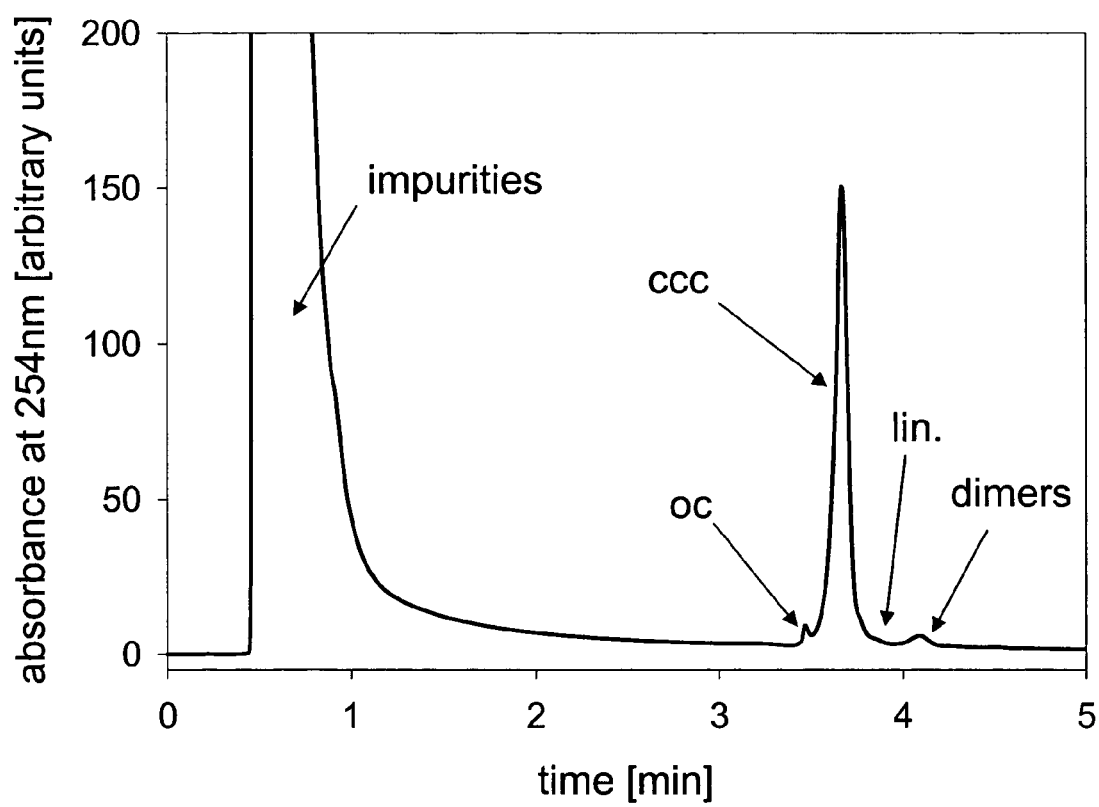
Figure 12:
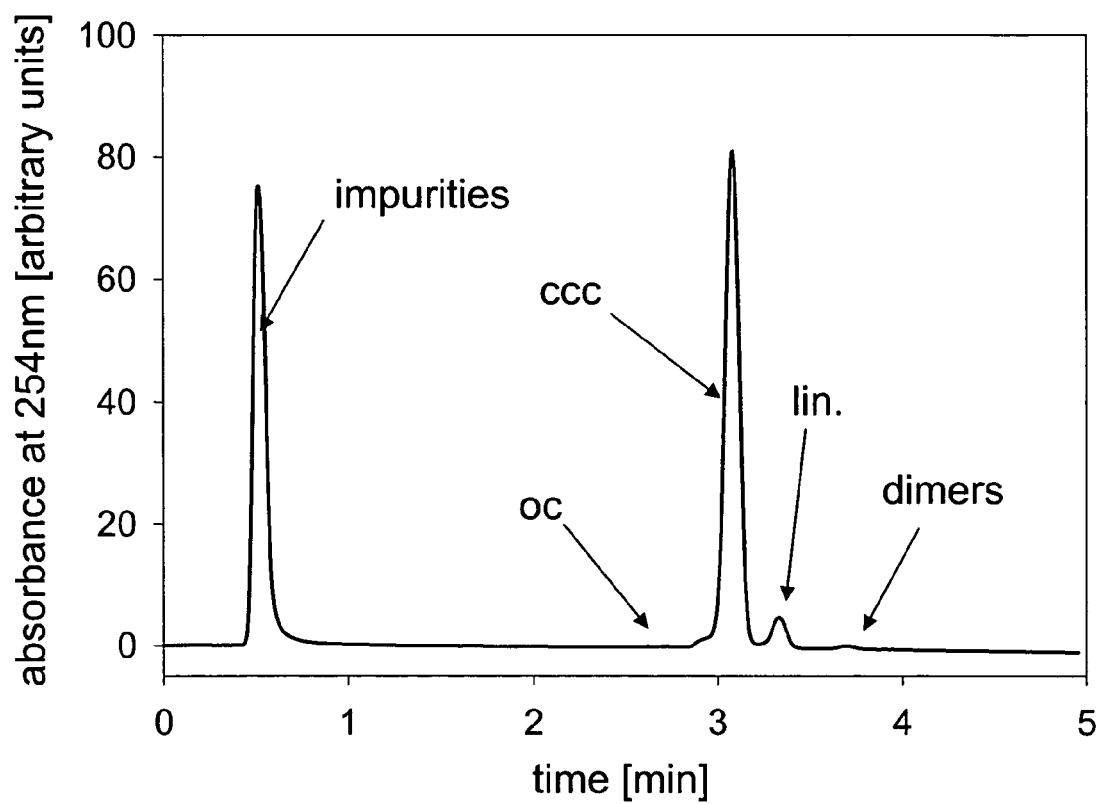
Figure 13:
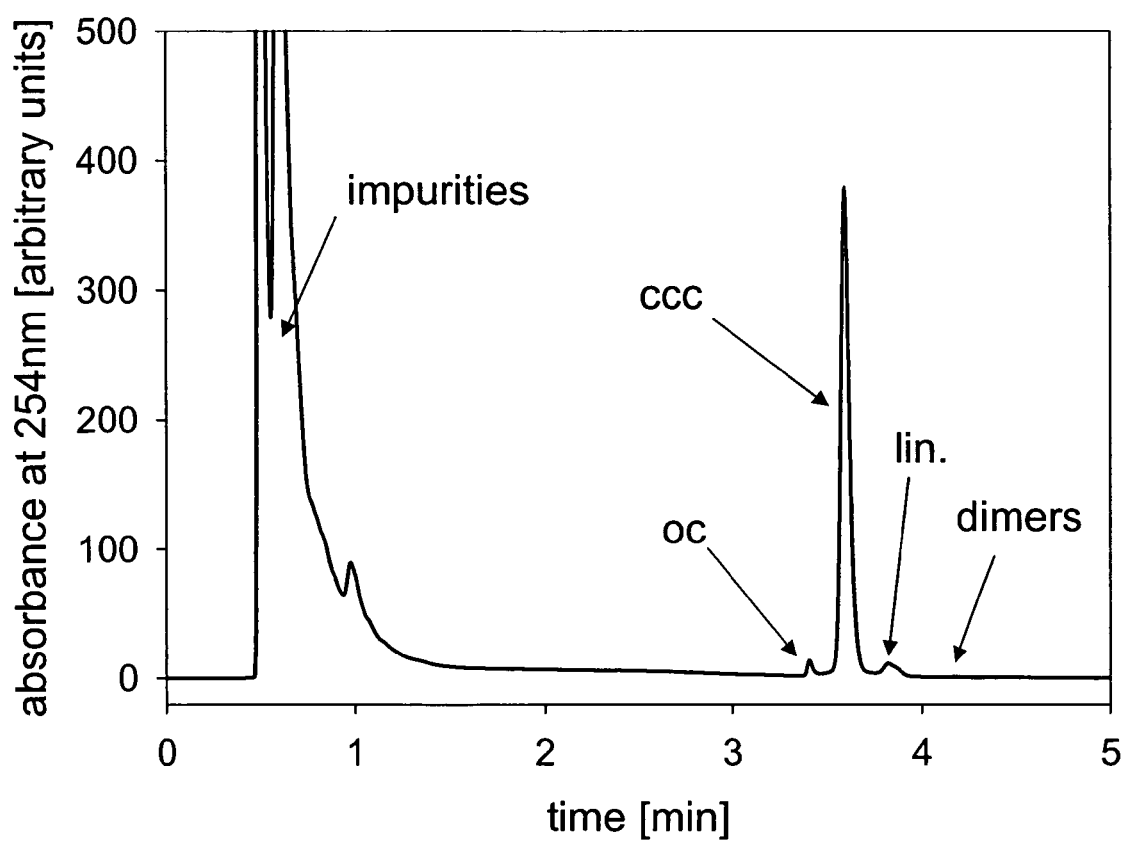

FIG. 10: Analytical HPLC chromatogram of a lysate obtained by the continuous method of the invention including the steps lysis, neutralization and clarification in the pilot device FIG. 11: Analytical HPLC chromatogram of a reference lysate obtained by a conventional method on the laboratory scale FIG. 12: Analytical HPLC chromatogram of a pool from the capture step obtained by the extended continuous method of the invention including the steps lysis, neutralization, clarification, conditioning, filtration and capturing FIG. 13: Analytical HPLC chromatogram of a lysate obtained by the continuous method of the invention including the steps lysis, neutralization and clarification in the up-scaled device.

Figure 14:
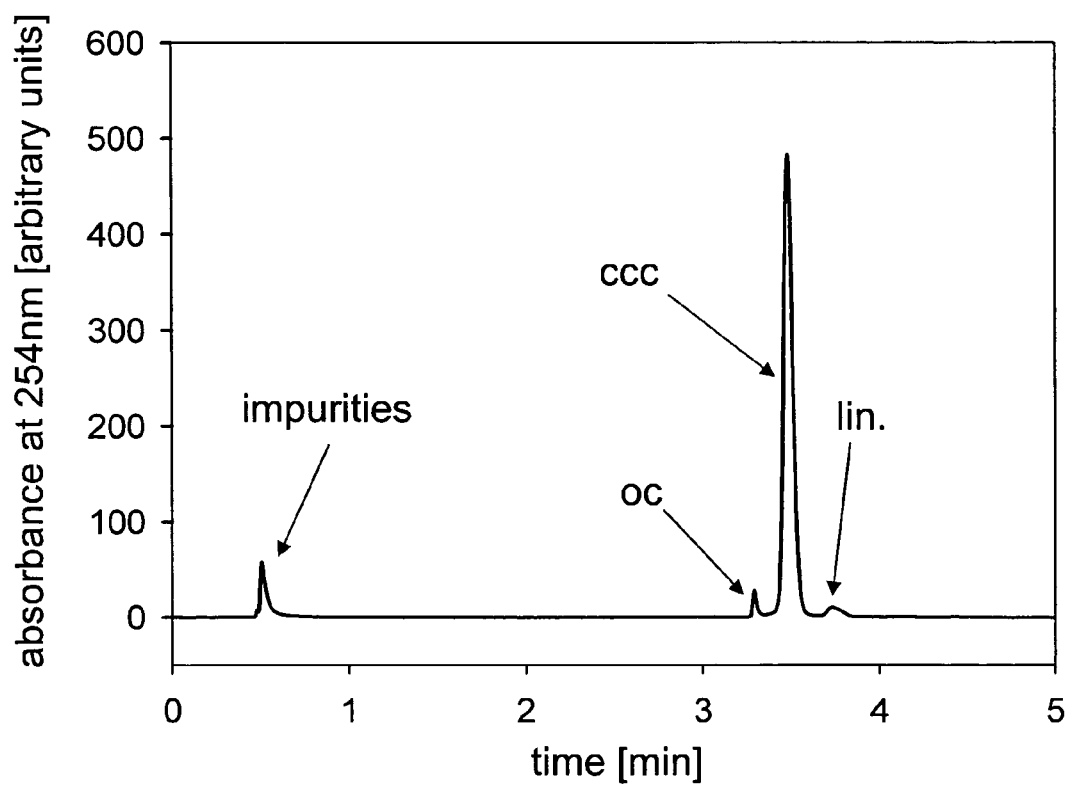

FIG. 14: Analytical HPLC chromatogram of a pool of the capture step. Lysate obtained by the continuous method of the invention including the steps lysis, neutralization and clarification in the up-scaled device.

Figure 15:
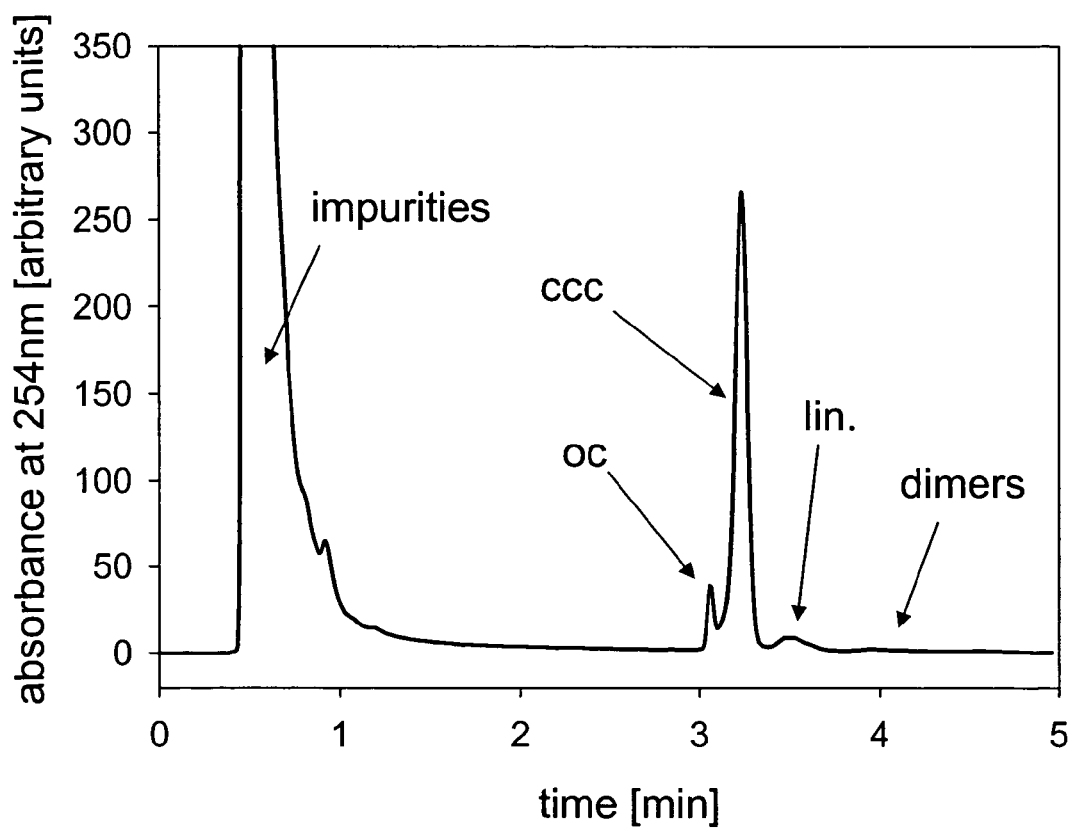

FIG. 15: Analytical HPLC chromatogram of a lysate obtained by the continuous method of the invention including the steps lysis, neutralization and clarification, which was concentrated by ultrafiltration.

DETAILED DESCRIPTION OF THE INVENTION

Steps a) to c) and step e) may be performed according to known methods, preferably according to methods that can be run continuously and automated.

a) Fermenting/Cultivating:
In the method of the invention, preferably *E. coli* is used as host, in particular when the biomolecule of interest is pDNA.

In one embodiment of the invention continuously operated devices, e.g. tube centrifuges or separators, are used for separating the cells from the cultivation medium. If the cells (the biomass) are frozen prior to further processing, the cells can be frozen directly after harvesting or after resuspension of the cells in a suitable buffer, typically a buffer containing 0.05 M Tris, 0.01 M EDTA at pH 8. In this case no resuspension buffer has to be added prior to alkaline lysis or it is required in lower amounts.

Biomass that is obtained in a fermentation, may be, before being further processed (resuspended, lysed, etc.), frozen, in particular cryo-pelleted. Cryo pelletation is an advantagous method to prepare cells for storage. Since this method guarantees fast freezing of the cells undesired temperature gradients, within the biomass, can be avoided. Slow freezing in a conventional freezer may lead to inhomogeneous freezing and the building of ice crystals, which may damage the cells and reduce their shelf life and the quality of the polynucleotide of interest. The same may be observed when the biomass is thawn again.

In a preferred embodiment, the biomass obtained in step a) is cryo-pelletized. With a cryo-pelletation system the fermentation broth can be directly frozen or after harvest and resuspension in a suitable ratio of resuspension buffer. Cryo-pelletation devices normally work with fluid gases in which the (stirred) material to freeze is applied dropwise and the resulting pellets continuously brought out of the system or/and avoided to agglomerate by slowly stirring inside. These devices are commercially available and have been used so far in the food industry in the production of ice cream or in the pharmaceutical industry for the storage of final products. The size of the pellets depends on the nozzle used for distribution of the material into the gas and the velocity of application. For the harvested biomass an average pellet size between 0.5 and 2 cm was found to be suitable. After cryo-pelletation the pellets may be stored in a conventional freezer at −20-100° C. The method results in homogenous pellets that can be easily divided into several aliquots, which is another advantage compared to the conventional technique. For the processing of the biomass the aliquots can be thawn faster, due to the larger surface of the pellets compared to larger blocks. The thawing can be further accelerated when resuspension buffer at room temperature is added and this suspension is stirred with conventional stirrers.

In an embodiment of the invention, harvesting and resuspending the cells may be omitted, in this case the fermentation broth can be directly further processed in the lysis step b) without separation of cells and cultivation supernatant.

b) Disintegrating by Alkaline Lysis:

The harvested cells of step a) are either directly processed or thawn, if frozen before. Common to both procedures is that the harvested cells are resuspended in the resuspension buffer described in a) prior to the intrinsic cell disintegration step b).

Alternatively the fermentation broth obtained in step a) is directly further processed without harvest and resuspension of the cells. In this case, the cells may be disintegrated by directly conducting alkaline lysis (and optionally subsequent neutralization) in the fermentor or by introducing the fermentation broth into the lysis reactor.

(In the following, with respect to cell disintegration in step b), the term "cell suspension" is used for both the resuspended cells after harvest and the fermentation broth.)

In principle, step b) can be performed according to methods known per se, preferably according to methods that are gentle and can be run in a continuous and automated mode.

In a preferred embodiment, in step b) the cell suspension and the alkaline lysis solution are allowed to flow through a lysis reactor that is essentially completely filled with particulate material, thereby contacting and mixing the cell suspension with the alkaline lysis solution.

Preferably, the cell suspension and the alkaline lysis solution are combined, without further mixing, before entering the lysis reactor, thus forming a single flow that is thoroughly mixed when flowing through the particulate material in the lysis reactor and achieving very gentle lysis. By avoiding disadvantageous shear forces, plasmid DNA quality is maintained at a very high level. Furthermore, the yield of supercoiled plasmid DNA is higher as compared to conventional methods. This is due to two reasons: Firstly, degradation, which can occur when using harsher mixing conditions and devices, is reduced. Secondly, due to the homogenous mixing, the cells are completely disintegrated (releasing the whole pDNA-amount), avoiding local pH-extremes, which may also result in degradation of the target plasmid DNA molecule.

Alternatively, the cell suspension is introduced into the reactor simultaneously with the lysis solution, preferably through inlets that are as close as possible to each other.

Preferably, in both embodiments, the cell suspension and the lysis solution are transported, e.g. by pumps or pressurized gas, at a defined ratio of flow rates, thereby achieving a constant ratio of cell suspension and lysis solution volumes.

In terms of the lysis reaction per se, step b) in the preferred embodiment of the present invention, is performed according to methods known in the art, using an alkaline lysis solution that contains a detergent. A typical lysing solution consists of NaOH (0.2 M) and SDS (1%), but also other alkaline solutions and other detergents can be used (see e.g. WO 97/29190).

The lysis reactor, which is also a subject of the present invention, is a flow-through container that is filled with the particulate material, preferably a hollow body formed as a cylinder or tube, in particular a glass or stainless steel tube. The tube may also be made of plastic or any other material acceptable for biopharmaceutical production. The particles, in particular beads, which are preferably made of glass, but can also consist of stainless steel, plastic or other materials, are packed into the reactor in a random way, so that it is completely or essentially completely filled, with free space of random size and shape between the particles. Due to this, functionality of the lysis reactor is independent of whether and in which way the flows of the two solutions have been connected before they enter the lysis reactor. It is even possible that the solutions are combined directly in the device. The beads can be of equal or different diameter, their size depending on the scale on which the process is operated, generally ranging from ca. 1 to ca. 100 mm. In a preferred embodiment the diameter of the beads is 5 mm. Instead of beads, other filling elements that provide efficient mixing can be used, e.g. rods, fibrous material like fiberglass, grids in shifted layers, nets, or particles of irregular shape. Mixing of the solutions is not limited by the direction of the flow through the device, it may be performed in any direction, e.g. vertically upwards or downwards, horizontally or in any angle.

The parameters of step b) and the dimensions of the device used therein are advantageously designed such that homogenous mixing is guaranteed and contact time is kept in a certain range from 5 seconds to 5 minutes or more, preferably at 1 to 3 minutes, in order to avoid denaturation of the desired polynucleotide. These parameters can be adjusted by the dimension of the device, the free volume between the packed beads and the flow rate. The contact time for adequate alkaline lysis of cells depends on the host strain and is independent of the biomolecule of interest, in the case of pDNA it is independent of plasmid size or the plasmid copy number (PCN).

c) Neutralizing/Precipitating:

Also this step may, in principle, be performed according to methods known per se, preferably according to methods that are gentle and can be run in a continuous and automated mode.

In a preferred embodiment, in the neutralization step c) the lysed cell solution is mixed with the neutralizing solution in a continuous, preferably automated manner. This is accomplished by combining the lysed cell solution and the neutralizing solution, at a constant ratio of the flow rates (e.g. by means of a T connector or Y connector) and ensuring mixing and neutralizing/precipitating during transportation of the reaction mixture between the lysis reactor and the subsequent clarification reactor.

For this purpose, a novel neutralization reactor, which is also subject of the invention, is used. This reactor consists of a connector means and a tubing system, which is designed such that homogenous mixing of lysed cell solution and neutralization solution is guaranteed and the newly formed flocks of the precipitate are not destroyed by shear forces. The tubing system may be rigid or flexible, preferably it is in the form of a coil, the dimension (diameter and overall length of the tubing and diameter of the coil) depending on the scale of the process. The tube can be made of any material acceptable for biopharmaceutical production, preferably plastic or stainless steel.

According to a preferred embodiment, the flow paths of the lysed cell solution and the neutralization solution are combined by a conventional connector, e.g. a T connector or a Y connector. Once the lysed cell solution is contacted with the neutralization solution, the formation of the flocks starts. The resulting mixture is then transported, preferably by pumps or pressurized gas, through the tubing system. Depending on the scale of the process, the inner diameter of the tubing is in the range of ca. 3 to ca. 100 mm, preferably greater than 8 mm in order to avoid shear of the flocks at the tubing wall. The orientation of the flow may be upwards, downwards, horizontally or in any other direction, preferably in the form of a spiral. A mixing distance of 30 cm to several meters allows gentle and complete mixing of the solutions and thus precipitating the cell-derived impurities. The mixing distance, the inner diameter of the tube as well as the retention time in the mixing device effect the quality of mixing and the formation of the precipitate.

Typically a buffered solution with acidic pH and high salt concentration is used for neutralization. Preferable this solution consists of 3 M potassium acetate (KAc) at pH 5.5. But also other neutralizing salts can be used or added.

d) Separating/Clarifying and Optionally Washing:

In step d) the mixture obtained in step c) comprising the precipitate and the lysate (which in the case of pDNA and usually in the case of proteins contains the biomolecule of interest) is allowed to gently flow downward through a clarification reactor that contains, in its lower part, a retention layer, whereby the precipitate is retained on top of and within the retention layer and the cleared lysate leaves the reactor through an outlet in the bottom of the reactor. If the aeration valve on the top of the clarification reactor is, which is usually the case, completely closed, the free volume in the clarification reactor decreases in the course of the process due to the increasing level of the flock/lysate mixture. Therefore, the pressure in the reactor increases constantly over time. This results in a constant outflow that is obtained without further handling.

In a preferred embodiment, in step d) the retention layer in the clarification reactor is composed of a particulate material.

In another embodiment, to accelerate the process, increasing pressure is applied to the mixture in the clarification reactor, e.g. by applying pressurized gas, in particular air, from the top of the reactor. Normally, application of pressure is not required at the beginning of the process but when the process further proceeds. Usually, the pressure is increased stepwise, e.g. in the range of 0.2 bar, the intervals being defined by the points of time when predetermined aliquots of the precipitate/lysate-mixture have entered the reactor. Alternatively, the pressure may be increased continuously.

The clarification reactor, in which the mixture containing the flocks (which are, in the case of pDNA, a co-precipitate of gDNA, proteins, cell debris and SDS) is further processed and which is also subject of the invention, can be made of glass, stainless steel, plastic or any other material that is acceptable for pharmaceutical production. A preferred shape is cylindrical, but in principle every other hollow body is possible. Step d) in the method of the invention is independent of the shape of the reactor.

The reactor has an inlet at the top or at any other position above the retention layer and has an outlet at the bottom, underneath the retention layer. Inside the reactor, preferably in the center, there is a distribution means that reaches to the surface of the retention layer and evenly and gently, without destroying the flocks, distributes the mixture into the clarification reactor. This distributor is connected with the supply means that transports the mixture through the inlet, or it represents an extension of the supply means. The distributor may be in the form of a tube or coil with apertures like slots, which may be in any direction, e.g. vertically or horizontally, or perforations or other apertures, or in the form of a chute, it may be a simple rod or a combination of two or more identical or different of such distributing devices, that are preferably arranged vertically or slightly inclined. The distributor has apertures over at least 10% of its total length, the apertured section being located above the retention layer. Preferably, the distributor carries apertures over its entire length.

In a preferred embodiment, the distributor is a perforated tube that reaches to the surface of the retention layer and has a rod in its center. In case the retention layer consists of particulate filling material, this may be of regular (e.g spherical, cylindric, in form of plates) or irregular (sandy, gritty . . . ) shape, preferably, in the form of beads.

The beads may be of identical or different diameter, ranging from 0.1 to 10 mm. In a preferred embodiment the diameter of the beads is 1 mm.

If the retention elements are beads, they are preferably made of glass, but they may also be made of stainless steel, plastic or other materials that are acceptable for biopharmaceutical production. The particles are packed into the reactor in a random way up to a certain height, providing sufficient clarification The volume that the retention material occupies is not critical as long as it ensures that the residual reactor volume is sufficiently large to collect the flock volume to be processed. By way of example, independent of the reactor base, the height of the retention material should be in the range of 1-15 cm, in particular 2-5 cm, for a total reactor height of 40-100 cm. The height of the filling material in the reactor depends on the specific size and shape of the filling material itself and its capacity to retain the flocks. The optimum filling height has to be determined empirically for the selected retention material: Due to their larger retention capacity, a thinner layer is necessary for particles or retention material with smaller pores as compared to larger particles or material with larger pores.

Preferably, the filling material takes approximately at least 5% to a maximum of 30% of the total reactor volume.

In case of particulate retention material, the particles are held back by a device in the outlet, e.g. a frit. Naturally, this flit must have pores smaller than the particles used in the reactor. The frit may be made of polypropylene or any other suitable material with an average pore size of 10 to 200 µm, preferably 30-100 µm.

The outlet of the clarification reactor may be extended by a tubing. In this case, the frit may be situated distant from the outlet inside the tubing; thus the tubing above the frit is filled with the retention material.

Instead of particulate retention elements, the bottom of the clarification reactor may be filled with rigid retention material, e.g. sinter plates, preferably made of glass and having a pore size from apx. 100 µm to apx. 500 µm. In a specific embodiment, a sinter plate with larger pores can be placed on top of one with smaller pores.

In the course of the separation process, the flocks float in the reactor whereas the clear lysate runs through the retention layer. Flocks that are not floating are retained by the retention layer.

In a preferred embodiment, connections for supply of compressed gas, e.g. air, are located in the top of the clarification reactor. In this case, the clarification reactor has to be pressure-resistant (since the pressure in the reactor increases even if no compressed gas is supplied, when the aeration valve on the top is closed, the reactor should be pressure proof up to 6 bar). By applying compressed gas, the clarification process can be accelerated, which is a very gentle method of increasing the outlet flow and at the same time avoiding shear forces that might damage the biomolecule.

The pressure has to be in a range such that the flocks are not pressed through the retention material, especially at the end of the procedure. Preferably, the applied pressure is in the range of 0.1 to 3 bar, most preferred up to 2 bar. The resulting neutralized lysate is visually clear and can directly be further captured and processed, usually by chromatographic techniques.

At the end of separation/clarifying step d), the residual fluid between the flocks, which are then present on top of and possibly also within the retention layer, in particular when using larger particulate material or rigid retetention material with larger pores, may be recovered by applying pressure. This leads to drainage of the flocks.

This provides an advantage in that the residual fluid between the flocks that contains the biomolecule of interest, e.g. plasmid DNA, and that can normally not, or only insufficiently be recovered, is obtained at maximum yield. Thus, practically the entire lysate is obtained as a clear solution.

In addition, one or more wash steps may be inserted between steps d) and e). In this case, at the end of step d), the flocks are washed with a suitable buffer that does not re-dissolve the flocks, e.g. 3 M potassium acetate at pH 5.5, or a mixture of the solutions used in the resuspension, lysis (without SDS) and neutralization step, e.g. at a ratio of 1:1:1, by pumping the solution successively or simultaneously in either of the two or in both directions through the flocks, i.e. from the inlet and/or the outlet of the reactor. If pumping is done from the inlet, the wash step can be continuous or batchwise. If it is done from the outlet, which is preferred, the wash buffer may, but does not need to, be pumped into the tank up to the inlet. Then the solution is recovered at the outlet, applying the same method as described above (compressed air).

e) Purifying:

A process following steps a) to d) of the invention facilitates isolating (capturing) and purifying of the biomolecule of interest in the subsequent chromatographic steps.

Before capturing/purification by means of a resin, it may be necessary to adjust the parameters of the solution (like salt composition, conductivity, pH-value) to ensure binding of the desired biomolecule to the chromatographic support, usually a resin (this step is, in the meaning of the present invention, termed "conditioning step"). The simplest conditioning procedure is dilution of the cleared lysate with water or low salt buffer, especially in case the chromatographic resin in the subsequent capture step is achieved by anion exchange chromatography (WO 97/29190 A1). Furthermore, in particular when hydrophobic interaction chromatography is used as first purification step, a high concentration salt solution may be added and the possibly resulting precipitate (which is present if a certain salt concentration in the solution is exceeded) separated by filtration or centrifugation (WO 02/04027 A1). In the case ammonium sulfate is used in high concentrations, this treatment reduces the RNA content (WO 98/11208 A1).

For capturing and purification several steps are applied to obtain a highly purified biomolecule which meets the requirements for pharmaceuticals. As for the previous steps, enzymes, detergents and organic solvents should be avoided. Isolation and purification are performed according to methods known in the art, in particular by a combination of different chromatographic techniques (anion exchange chromatography AIEC, hydrophobic interaction chromatography HIC, size exclusiton chromatography (SEC), ultra(dia)filtration, filtration or precipitation and extraction. A method that may advantageously be used, in particular for obtaining pDNA for therapeutic applications, comprises a combination of two steps that are based on different chromatographic principles, in which either of the two steps is selected from hydrophobic interaction chromatography (HIC), polar interaction chromatography (PIC) and anion exchange chromatography (AIEC) and in which at least in one of the two steps, preferably in both steps, the chromatographic support is a porous monolithic bed, preferably a rigid methacrylate-based monolith in the form of a monolithic column. Suitable monolithic columns are commercially available under the trademark CIM® from BIA Separations). This purification process process may advantageously be performed with a chromatographic support in the form of a single monolithic bed comprising a tube-in-a-tube system, the outer and inner tube carrying different functional moieties. In such a system one of the monolithic tubes represents the support for the chromatographic principle of one step and the other tube represents the support for the chromatographic principle of the other step. Preferably, the capturing/purification step can be operated in a batchwise mode or in a quasi-continuous or continuous mode, employing technologies such as annular chromatography, carousel chromatography or a simulated moving bed process.

The process of the invention is suited for, but not limited to, biomolecules that are sensitive to shear forces, preferably to polynucleotides, in particular plasmid DNA, and large proteins, e.g. antibodies.

The process of the invention can be used for any biomolecule of interest. For the production of proteins, it may be designed such that the specific needs of the protein of interest are met. The method of the invention is independent of the fermentation process and of the source of the protein (e.g. bacteria, yeast).

The choice of specific methods suitable for cell disintegration and the following processing steps is strongly influenced by the protein's state in the cells after fermentation:

If the protein is overexpressed, it may be present in the form of so-called "inclusion bodies". In this case, the treatment with e.g. strong alkali in combination with a reducing agent (e.g. DTT) during lysis results in a resolubilization of the protein, which is, at this stage, in its denatured form. To reconstitute the protein's native structure, refolding can be achieved by neutralization (e.g. by addition of phosphoric acid) in the neutralization reactor or in a second reactor similar to the lysis reactor. Insoluble components are separated from the protein-containing solution in the clarification reactor.

In the case the protein of interest is soluble in the cell, the cells are disintegrated in the lysis reactor in a similar manner as described above.

In the lysis reactor, the conditions (contact time, concentration of the lysis solution) may be chosen in a way that the protein stays soluble or, alternatively, the parameters are set to specifically denature and precipitate the protein. In the first case, the solution is further processed in the neutralization reactor (which, in terms of construction, is similar to the lysis reactor or the neutralization reactor used for polynucleotides) and the clarification reactor, as described for solubilized inclusion bodies. If the protein is in its denatured state, precipitation can either already take place in the lysis reactor or afterwards in the neutralization reactor (by addition of a neutralizing and/or precipitating agent). In both cases, the conditions for the precipitation are preferably chosen to specifically precipitate the protein of interest (while undesired impurities like e.g. RNA, endotoxins, and DNA stay soluble). The precipitate is subsequently separated from the solution in the clarification reactor. Afterwards, the precipitate is either removed from the clarification reactor (e.g. by sucking off or flushing out with an appropriate buffer) or directly further processed in this device. After it has been removed from the reactor, the precipitate is resolubilized in a separate container using a suitable buffer, which is empirically determined on a case-by-case basis. In the case the precipitate remains in the clarification reactor, resolubilization is done there (by addition of a suitable buffer and optionally mixing). As soon as the precipitate (especially the protein of interest) is resolubilized, it can easily be removed from the clarification reactor through the outlet in the bottom.

Common to all variations of the method of the invention in the production of proteins are the options for further processing the resulting protein solution. Beside additional refolding steps, the same steps as described for processing of polynucleotide solutions (continuous or non continuous concentration, conditioning, filtration, capturing) may take place.

The process of the invention meets all regulatory requirements for the production of therapeutic biomolecules. When applied to polynucleotides, the method of the invention yields—provided the fermentation step has been optimized to provide high quality raw material—high proportion of plasmid DNA in the ccc form and a low proportion of proteins and chromosomal DNA. The process neither requires the use of enzymes like RNase and lysozyme nor the use of detergents except in lysis step b).

The process of the invention is scalable for processing large amounts of polynucleotide containing cells, it may be operated on a "manufacturing scale", to typically process more than 100 grams wet cells, and yielding amounts from 0.1 g to several 100 g up to kg of the polynucleotide of interest that meet the demands for clinical trials as well as for market supply.

The applicability of the process is not limited or restricted with regard to size, sequence or the function of the biomolecule of interest. A polynucleotide of interest may be a DNA or RNA molecule with a size ranging from 0.1 to approximately 100 kb or higher. Preferably, the polynucleotide of interest is circular DNA, i.e. plasmid DNA with a size of preferably 1 to 20 kbp.

The process and the devices of the invention are not limited with regard to the cell source from which a biomolecule of interest is to be obtained.

The process can be easily implemented and is flexible with regard to automatization and desired scale; adjustment of the flows and the reaction times can be achieved by commercially available pump and pressure systems that ensure steady flows and a low impact of mechanical stress.

Another advantage of the present invention is that the devices are sanitizeable, depyrogenysable and allow cleaning in place (CIP) and steaming in place (SIP).

The method and apparatus employed therein provides a controllable and consistent performance in a closed system, allowing direct further processing of the continuously produced lysate obtained after clarification, e.g. loading it to a chromatography column or allowing online conditioning of the lysate prior to column loading. After clarification, there may be an intermediate concentration step before conditioning or loading onto the chromatographic column.

In the process of the present invention, irrespective of whether steps a) is performed batchwise or in a continuous mode, each subsequent step may be run in a continuous and automated mode. Preferably, at least a combination of two steps selected from steps b) to e) is run continuously connecting the individual steps.

In the case the lysis step b) is the automated step, it is independent of how the cell suspension has been obtained (batchwise or continuous operation, direct use of fermentation broth or harvest and resuspension, optionally after freezing). It is also independent of the host from which the lysate has been obtained.

In the case the neutralization step c) is the automated step, the application is independent of how the processed alkaline lysed cell solution has been prepared (e.g. batchwise or continuous). In a preferred embodiment the collector tank is designed in the same way as described for the clarification step.

In the case the clarification step d) is the automated step, the application is independent of how the processed neutralized lysed cell solution containing flocks has been prepared (e.g. batchwise or continous). It is also independent of how the resulting clarified lysate is further processed.

In a preferred embodiment, the outflow of the clarification reactor is combined with the flow of the solution necessary for the next processing step (conditioning solution) by means of a connector, e.g. a T- or Y-connector or directly in a mixing device. The two solutions may be pumped by conventional pumps.

In another embodiment only the flow rate of the second solution is adjusted to the flow-rate of the lysate leaving the clarification reactor. The mixing device for this purpose may be a device filled with beads like the one described for the automated lysis step or a tubing system like the one described for the neutralization step. Such a setup may be used if conditioning of the lysate for the first chromatographic step is necessary. For example, a solution of ammonium sulfate (or simply water) can be added in this way.

In another embodiment, the process also contains an intermediate concentration step: as soon as a sufficient volume of the lysate leaving the clarification reactor is present, the lysate is concentrated, e.g. by means of ultrafiltration, prior to conditioning and/or loading onto the chromatography column. Concentration may be done in one or more passages. In the latter case, the concentration step as such may be in a continuous or batchwise mode. If only one passage takes place, the retentate (e.g. containing the pDNA) may subsequently be directly conditioned or loaded to a chromatography column. In the case of several passages, the retentate is recycled until the desired final volume/concentration is reached, and subsequently further processed. For this concentration step, conventional devices can be used, e.g. membranes in form of cassettes or hollow fibres. The cut-off of suitable membranes depends on the size of the biomolecule processed. For pDNA, usually membranes with a cut-off between 10 and 300 kDa are used.

In a preferred embodiment, the lysis reactor and the neutralization reactor are combined to form a two-step automated system. In this case, the outflow of the lysis reactor is connected and mixed with the flow of the neutralization solution in the manner described for the automated neutralization step. By this, the flow rate of the pumped neutralization solution is adjusted to the flowrate of the outflow of the lysis reactor.

In another preferred embodiment the neutralization reactor and the clarification reactor are combined to form a two-step automated system. In this case, the outflow of the neutralization reactor is connected with the automated clarification reactor of the invention. In this case, the pressure of the compressed air has to be adjusted such that the outflow of the reactor is kept constant. This may be achieved by measuring the fluid level by means of an integrated floater or similarly by measuring the flow at the outlet. Also other systems like light barriers are applicable. By means of an electronic connection to the pressure gauge the pressure can be adjusted steplessly according to the fluid level or the outlet flow.

In another embodiment the lysis step and the clarification step are connected by directly connecting the two reactors without an intermediate distinct neutralization step. Neutralization may in this case be carried out in the clarification reactor. In this embodiment, the outlet of the reactor is closed at first and the lysed cell solution is mixed with a certain volume of neutralization solution by mixing slowly with a stirrer or introducing air through the distributor from the top or from an inlet in the bottom of the reactor. At the end of neutralization, automated clarification takes place in the same manner as described above.

In an even more preferred embodiment, the whole system is fully automated by employing at least all steps b) to d) and optionally, in addition, step a) and/or e) in a continous system. In this embodiment, the outflow of the lysis reactor is directly connected with the neutralization device and the outflow of the neutralization device is directly connected with the clarification reactor. The design for the individual connections and devices is the same as described above for the two-step automated systems.

In a most preferred embodiment, the fully automated system is connected to an optional automated conditioning step (and device). This embodiment allows continous mixing of the clarified lysate that leaves the clarification reactor with a conditioning solution (e.g. an ammonium sulphate solution). As described above, such conditioning step may be necessary to prepare the polynucleotide containing lysate for the subsequent (chromatographic) purification steps (e.g. hydrophobic interaction chromatography).

Adding such a conditioning step results in an extension of the automated three-step system to a continuous four-step system. In this embodiment, a conditioning solution can be continuously mixed with the clarified lysate using a device, which is preferably of the same type as the lysis reactor. This device was found to be most gentle for continous mixing of solutions containing polynucleotides that are sensitive to shear forces. Yet also other devices (e.g. as described for the neutralization step) can be utilized for this purpose, e.g. conventional static mixers. The flow rate of the pump that pumps the conditioning solution can be adjusted to the flow rate of the outflow of the clarification reactor by installing a flow measurement unit. The pump can be connected with this unit and thus regulated, keeping the ratio of the flow rates of the two mixed solutions constant.

Between conditioning and capture step, an on-line filtration step may be inserted.

In yet another embodiment of the invention, an ultrafiltration step is added. By such an extension of the automated three-step system, the process represents a continuous four-step system. In this embodiment the resulting lysate of the previous steps is concentrated by ultrafiltration. While the permeate is discarded, the retentate is either directly further processed by the conditioning step and/or by the loading step (which means an extension of the continous system by one or two additional steps) or recycled until a desired final concentration/volume is reached. In the latter case, the resulting concentrate is further processed (conditioning and/or loading) after concentration is finished.

In another embodiment, the lysate flowing out of the clarification reactor may be directly loaded onto a chromatographic column, or it may be loaded onto the column after conditioning (with or without subsequent on-line filtration).

In all described embodiments utilizing the automated clarification step the obtained cleared lysate may either be collected in a suitable tank or directly further processed (e.g. by connecting the outflow of the clarification reactor with a chromatographic column). If a conditioning step is employed in this automated process, the conditioned lysate can either be collected in a suitable tank or directly further processed.

The method and devices of the invention are independent of the pumps used for pumping the solutions. In a special embodiment, the flow of the several suspensions and solutions is accomplished by air pressure in pressurized vessels instead of pumps.

Due to these advantages, the process and devices of the invention are suitable for cGMP (Current Good Manufacturing Practice) production of pharmaceutical grade pDNA. The process can be adapted to any source of pDNA, e.g. to any bacterial cell source. In particular due to the properties of the system, the process of the invention allows fast processing of large volumes, which is of major importance for processing cell lysates. Since the lysates contain various pDNA-degrading substances such as DNAses, process time is a key to high product quality and yield.

The process and device of the invention are suited for production of pDNA for use in humans and animals, e.g. for vaccination and gene therapy applications. Due to its high productivity, the process can be used for production of preclinical and clinical material as well as for market supply of a registered product.

Example 1

Production of pDNA-Containing *E. Coli* Cells

The pDNA containing *E. coli* biomass for the pilot scale runs was produced at 20 l or 200 l fermentation scale according to the following procedure (this description relates to the 20 l fermentation):

Pre-Culture

The working cell bank of a production strain of the plasmid pRZ-hMCP1 (*Escherichia coli* K12 JM108; ATTC no. 47107; plasmid size: 4892 kbp) was maintained in cryo vials (glycerol stocks) at −70° C. A cryo vial of the working cell bank was thawn at room temperature for 15 min and a 200 µl aliquot thereof was inoculated in a 1000 ml Erlenmeyer shake flask containing 200 ml autoclaved preculture medium (composition in gL-1: Vegetable Peptone/Oxoid 13.5; Bacto Yeast Extract/Difco 7.0; glycerol 15.0; NaCl 1.25; $MgSO_4*7H_2O$ 0.25; $K_2HPO_4$ 2.3; $KH_2PO_4$ 1.5). The preculture was incubated at 37°+0.5° C. and 150 rpm up to an optical density (OD 550) of 1-1.5.

Fermenter Preparation

A fermenter of a total volume of 30 l (continuous stirred tank reactor) was used for fermentation. Three of the medium components (in gL-1 final culture medium: Vegetable Peptone/Oxoid 13.5; Bacto Yeast Extract/Difco 7; glycerol 15) was heat sterilized inside the fermenter at 121° C. for 20 min. After cooling down the fermenter content to <40° C., a macro element solution (in gL-1 final culture medium: tri-Sodium citrate dihydrate 0.5; $KH_2PO_4$ 1.2; $(NH_4)_2SO_4$ 5.0; $MgSO_4*7H_2O$ 8.8; $Na_2HPO_4*12H_2O$ 2.2; $CaCl_2*2H_2O$ 0.26; $NH_4Cl$ 4.0) was sterile-filtered into the fermenter. By sterile filtration with a syringe, 5 ml of a 1% m/v thiamine solution and 1.5 ml of a trace element solution was transferred into the fermenter. The trace element solution consists of (in gL-1 solution): $CoCl_2*6H_2O$ 0.9; $CuSO_4*5H_2O$ 1.23; $FeSO_4*7H_2O$ 38.17; $MnSO_4*H_2O$ 1.82; $Na_2MoO_4*2H_2O$ 0.48; $NiSO_4*6H_2O$ 0.12; $ZnSO_4*7H_2O$ 5.14. The fermentation medium was filled up with sterile deionized water to the final working volume of 20 L.

Fermentation and Harvest of Cell Paste:

The total pre-culture volume of 200 ml was transferred into the fermenter under sterile conditions. The cultivation conditions were set as follows: aeration rate 20 l min−1=1 vvm; agitation rate 400 rpm, 37+0.5° C.; 0.5 bar; pH 7.0+0.2). The pH value was automatically controlled with 5 M NaOH and 25% m/v $H_2SO_4$. The concentration of dissolved oxygen (DO, $pO_2$) was maintained at >20% of saturation by automatic control of agitation rate (400-700 rpm).

Cultivation was terminated 12 h after inoculation of the fermenter. After cooling down the culture broth to <10° C., the cells were harvested by separating in an ice water-cooled tube centrifuge. The obtained cell paste was packaged and stored at −70° C.

The experiments were performed with pDNA containing *E. coli* biomass of different 20 l batch and fed-batch fermentations as well as of 200 L batch fermentations (two different hosts, four different plasmids).

Example 2

Figure 6:
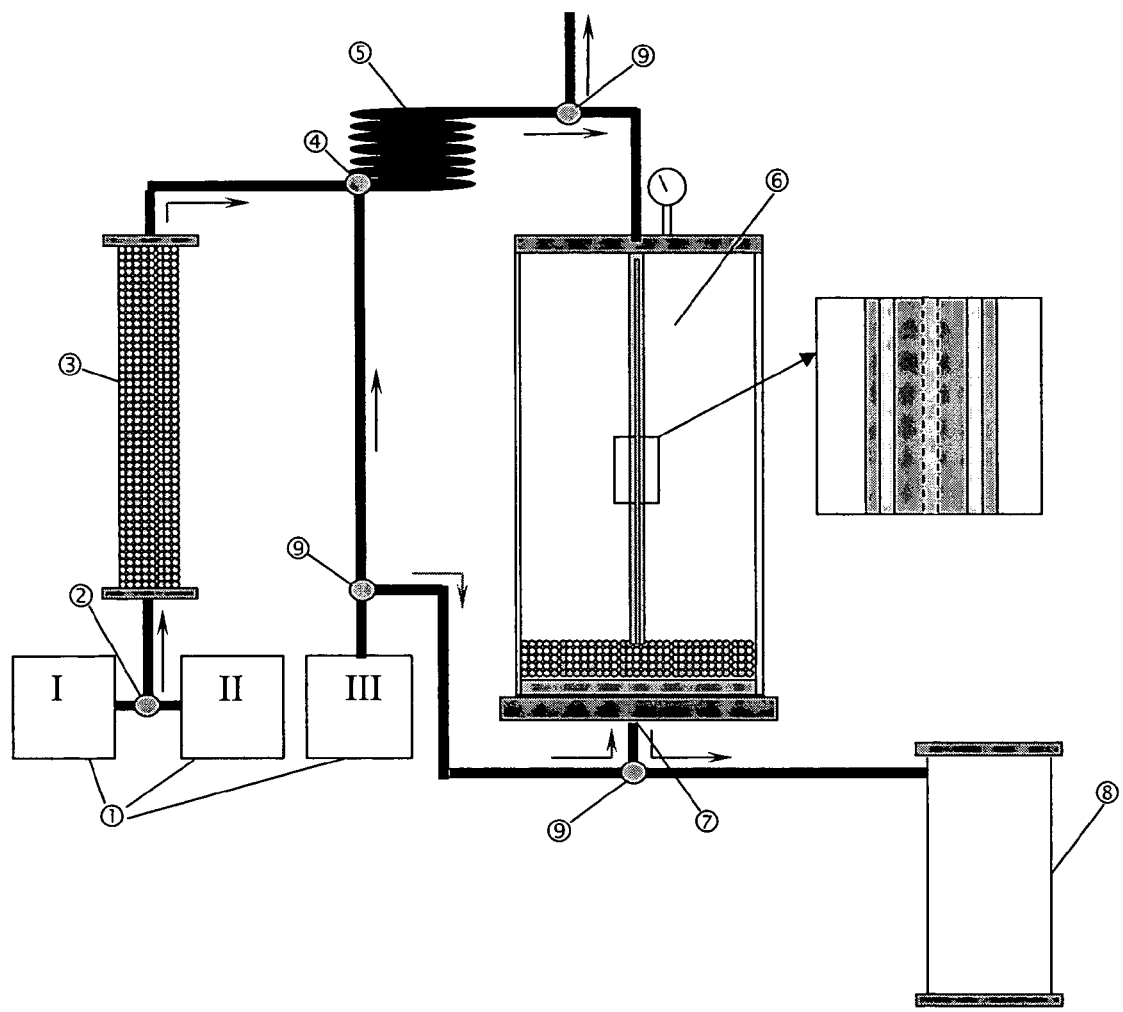

Setting up a Pilot Scale System for Continuous Alkaline Lysis, Neutralization and Clarification The setup of the pilot scale system for the continuous combination of alkaline lysis, neutralization and clarification on which the experiment of Example 3 is based, is shown in FIG. 7. FIG. 6 shows a schematic image of the components and the basic construction of the continuous three step combination. This Figure also relates in principle to the lab scale model (up to 100 g wet cell weight; used for preliminary experiments), to the up-scale variant (capable for handling up to 6 kg biomass) of the system and to the cGMP production system (up to 20 kg wet cell weight).

In FIG. 6, ① are three similar pumps, which transport the cell suspension (I), the lysis solution (II) and the neutralization solution (III). ② is the first meeting point constructed as a T-connection. ③ shows the lysis reactor (inner diameter: 6 cm, height 45 cm) filled with glass beads of 5 mm diameter. ④ indicates the second meeting point, again constructed as T connection. ⑤ shows the neutralization reactor (coiled polypropylene tubing of 12.5 mm inner diameter and 3.5 m length). ⑥ shows the clarification reactor constructed as a glass cylinder of 180 mm inner diameter and a height of 500 mm. In the center, a slotted stainless steel tube is built in to distribute the entering solution. On the top of the clarification reactor, a connection for pressurized gas and a pressure gauge is located. In the bottom of the clarification reactor the retention material (glass beads; diameter 0.75-1 mm) is filled in up to a height of 4-5 cm. Next to the retention layer ⑦ of the system is the outlet of the clarification reactor. ⑧ is the collector tank, which collects the cleared lysate that leaves the clarification reactor. ⑨ are conventional three-way valves to change the flow-paths to carry out degassing of the system and washing of the flocks in the clarification reactor.

Example 3

Utilization of the Pilot Scale System for Continuous Alkaline Lysis, Neutralization and Clarification 990 g wet biomass, prepared according to the above mentioned procedure (Example 1), was resuspended in 10 l of a buffer containing 0.05 M Tris-HCl, 0.01 M EDTA at pH 8, by mixing at room temperature (impeller stirrer) in a glass container for one hour.

Before the subsequent process was started, the lysis reactor and the neutralization reactor were degassed by pumping the suspensions and solutions with the 3 pumps.

Afterwards, all three pumps (pump I for the resuspended biomass, pump II for the lysis solution and pump III for the neutralization solution) were started simultaneously and adjusted to the same flow-rate (150 m/min) providing the desired contact time of the cells with the lysis solution and of the lysed cell solution with the neutralization solution in the respective reactors (lysis reactor, neutralization reactor).

Thereby the resuspended cells came into contact with the lysis solution (0.2 M NaOH, 1% SDS) at the first meeting point. The resulting stream was subsequently mixed homogeneously and contacted (1.5-2 min) in the lysis reactor by passing the glass beads. Directly after leaving the neutralization reactor, the now lysed cell solution was brought into contact with the neutralization solution (3 M potassium acetate at pH 5.5) at a second meeting point (T-connector). Both streams were mixed homogeneously in the following neutralization reactor and contacted (1-1.5 min). The mixture of the pDNA containing lysate and the precipitated impurities (flocks) were then transported into the clarification reactor by gently flowing down the special designed device. In this way, the mixture reaches the retention material in the bottom part of the reactor. Later the mixture is distributed on the surface of the lysate/flock-mixture that is already present in the reactor, with the majority of flocks floating. When the clarification reactor is filled up to 10 cm (above the retention material), the outlet of the reactor (which was closed so far) was opened to recover the cleared lysate at the outlet. Thereby the flocks are retained by the retention material. To accelerate the process, the pressure was increased stepwise (0.25 bar/2 l lysate) by introducing pressurized air to ensure constant outflow from the reactor. At the end, the system was washed with 1 l of the respective solutions (without cells) in order to recover the residual cells in the system in the form of lysed cells. The residual mixture in the clarification reactor was exposed to a maximum of 2 bar pressure and the lysate recovered to the largest possible extent, while the flocks stayed in the reactor. To also recover the pDNA containing lysate between the flocks, a gentle washing procedure was applied. Neutralization solution was pumped from the outlet of the clarification reactor into the device and through the precipitate. After this, the flocks were drained by exposing the mixture of flocks and wash-solution to an overpressure of up to 2 bar. The cleared lysate including the wash fraction was further processed by several subsequent chromatographic steps (HIC, AIEC using an 80 ml CIM® tube and SEC). Analysis was carried out by HPLC. As a reference sample, an aliquot of the resuspended cells equal to 1 g wet biomass was lysed and neutralized in a small tube according to the conventional lab-scale procedure, clarification being carried out by centrifugation (12.000 g). This sample was used to calculate the yield of the pilot-scale process and to compare homogeneity (criterion for smoothness and quality). In addition the purity of the pDNA-solution could be approximated (HPLC).

The comparison of the reference lysate and the lysate obtained from the continuous system (Table 1) shows that the results of the lab-scale lysis, that is known to be very gentle, and of the novel pilot-scale-system were comparable.

TABLE 1

|  | mg pDNA/ |  | Homogeneity | | |
|---|---|---|---|---|---|
|  | g WCP | Purity | oc | ccc | unid. |
| Reference lysate | 1.667 mg | 4.0% | 2.1% | 89.9% | 8.0% |
| Lysate of continuous system | 1.694 mg | 5.0% | 2.3% | 90.0% | 7.7% |

Example 4

Setting up an Up-Scaled System and a cGMP Production System for Continuous Alkaline Lysis, Neutralization and Clarification The principle construction of the up-scaled system and of the system for cGMP production is similar to the pilot scale system described in Example 2. FIG. 8 shows the up-scaled system, while FIG. 9 displays the cGMP-production system. The dimensions of the systems were adapted such that key parameters like linear velocity, contact time and process time are kept in a range comparable to the pilot system when larger amounts of resuspended cells need to be processed.

The stainless steel lysis reactor of the up-scaled system has an inner diameter of 10 cm and a height of 70 cm. The neutralization reactor is a polypropylene tubing of 19 mm inner diameter and 900 cm length, while the clarification reactor is constructed as a glass cylinder of 45 cm inner diameter and 50 cm height.

The lysis reactor of the production system was constructed as a stainless steel cylinder of 11 cm inner diameter and 84 cm height. The neutralization coil is made of a polypropylene-tubing of 25.4 mm inner diameter and 900 cm length. In this setup the clarification reactor consists also of stainless steel. A cylinder of 60 cm inner diameter and 65 cm height was constructed as a CIPable (CIP=cleaning in place) version.

Both systems are equipped with a flushing device in the clarification reactor to remove the majority of flocks of the reactor before the reactor is cleaned. In addition for safety reasons the systems are equipped with burst disks. The production system is especially designed for hygienic use and cleaning. All parts are CIPable and SIPable (SIP=steaming in place).

As retention material glass beads of 0.75-1 mm or 0.42-0.84 mm were used.

Example 5

Utilization of the Pilot System for Continuous Alkaline Lysis, Neutralization and Clarification and Further Continuous Conditioning, Filtration and Capturing As an option to extend the system of Example 2 and 3, the direct continuous connection of the subsequent steps conditioning, filtration and capturing was tested. Since hydrophobic interaction chromatography (HIC) was the first step of the chromatographic purification sequence, the lysate had to be conditioned by addition of ammonium sulfate to obtain binding of pDNA to the resin.

Therefore a lysate (of about 250 g wet cell paste, produced according to Example 1) obtained by the method described in Example 3 and by the device described in Example 2 was collected in a collection vessel. As soon as a sufficient volume of clarified lysate was present in this container, the automated conditioning-filtration-capturing procedure (according to FIG. 4) was started.

Two additional piston pumps were used in this extended setup. One piston pump was used to transport the cleared lysate at a flow rate of 28 mL/min while the other one, pumping a 4 M ammonium sulfate solution was adjusted to the double velocity (56 ml/min). Both streams were connected by a conventional Y-connector. The combined stream was entered to a mixing device similar to the lysis reactor, allowing sufficient homogenous mixing and contacting. As mixing device, a tube of 2.6 cm inner diameter and 100 cm length, filled with glass beads of 5 mm inner diameter was used. The contact time (here: about 2.5 minutes) was defined by the flow-rate through this conditioning reactor and by the free volume inside the reactor. During this conditioning procedure, precipitation of RNA and other impurities (e.g. endotoxines) took place. In order to load a solution free of particles to the chromatography column, a filter (4.5 μm pore size) was connected with the outlet of the conditioning reactor, thus providing an on-line filtration. The clear solution (containing the pDNA) leaving the filter was directly and continuously loaded onto the chromatography column (inner diameter 7 cm, bed height 25 cm) filled with Toyopearl Butyl 650 M. Under these conditions, pDNA was binding onto the resin and was separated from the majority of impurities during elution (performed after the entire conditioned lysate was loaded and a subsequent "wash"-step with an appropriate buffer). The result is displayed as HPLC-chromatogram of the resulting HIC-pool in FIG. 12. Impurities could be decreased to about 45% and that the oc pDNA (before in the range of 10%) was separated mostly.

Example 6

Utilization of the Up-Scaled System for Continuous Alkaline Lysis, Neutralization and Clarification To show scalability of the continuous three-step-system, the up-scaled system (described in Example 4) capable for up to 6 kg of wet cell paste was used to prepare a clarified lysate processing 5.4 kg wet cell paste produced according to Example 1 in a 200 L fermentation. After resuspension of the previously frozen biomass in 54.4 l resuspension buffer and degassing the system lysis, neutralization and clarification were carried out methodically as described in Example 3. The pumps were adjusted to 0.5 l/min providing a contact/mixing time of 1-1.5 minutes in the lysis and neutralization reactor. The resulting flock lysate mixture was separated in the clarification reactor, where the flocks were floating and retained by the retention material (0.42-0.84 mm). At the end of the process the retained flocks in the clarification reactor were washed from both sides with a buffer containing 0.017 M Tris-HCl, 0.003 M EDTA, 0.067 M NaOH and 1M potassium acetate at a flow rate of 1l/min. Finally the flocks were drained by applying 2.3 bar over pressure (pressurized air). The result is shown as analytical HPLC-chromatogram in FIG. 13. The obtained clarified lysate was further (stepwise) processed by the conditioning step (including filtration) and capturing (HIC). FIG. 14 shows the analytical HPLC chromatogram of the pool from the first chromatography step. The homogeneity of the lysate was about 93.5% and the approximated purity (roughly estimated by HPLC) about 10% while the HIC-pool showed a homogeneity of about 94% and an approximated purity of about 92%.

Example 7

Utilization of the Lab Scale System for Continuous Alkaline Lysis, Neutralization and Clarification Followed by Concentration, Conditioning and Capturing The concentration of lysate leads to a reduction of the volume of 4 M ammonium sulfate solution (if HIC is the following chromatography step) needed for conditioning and the duration of column loading. The clarified lysate was concentrated with a hollow fiber membrane (UFP-100-E4X2MA, Quix Stand) of Amersham Biosciences (100 kDa cut off).

For this Example, 70 g biomass as obtained by the method described in Example 1 was processed according to the description in Example 2 in the lab scale system (pumps: 15 ml/min; contact time: ~1 min). The resulting lysate was collected in a glass vessel. The glass vessel was connected with a peristaltic pump to feed the ultrafiltration membrane. After 100 ml of lysate were collected in the glass vessel ultrafiltration was started and continuously continued. Therefore the pump speed and the trans membrane pressure (~0.3-0.4 bar) were adjusted in a way that permeate and retentate flow were similar (20 ml/min respectively) resulting in a pDNA-concentration factor of 2-fold in the retentate. The obtained retentate is shown in FIG. 15 as analytical HPLC-chromatogram. While the lysis took 50 minutes (without washing of the flocks) the parallel concentration took about 60 minutes (to be sure not to run out of lysate). The retentate was collected in an intermediate vessel, which was used as feed tank for the following continuous steps conditioning, filtration and capturing, which are described in Example 5. The flow-rate of the pumped concentrated lysate (retentate) was therefore adjusted to 15 ml/min and for the ammonium sulfate solution to 30 ml/min). The column used for capturing had an inner diameter of 5 cm and a bed height of 25 cm).

What is claimed is:

1. A method of purifying a polynucleotide of interest from host cells comprising the polynucleotide of interest using an automated or semi-automated device, wherein the device comprises a lysis reactor, a neutralization reactor and a clarification reactor fluidly connected to one another, the method comprising:

a) providing a cell suspension of the host cells that have been cultivated to produce the polynucleotide of interest, wherein the cell suspension is a fermentation broth within which the host cells were cultivated or a re-suspension of the cultivated host cells that were harvested from the fermentation broth;

b) introducing a flow of the cell suspension and a flow of an alkaline lysis solution into the lysis reactor, the lysis reactor containing filling elements made of glass, plastic, stainless steel or fibrous material, such that the flow of the cell suspension and the flow of the lysis solution through the lysis reactor filling elements provides homogenous mixing of the flows in the absence of shear forces and whereby the cultivated host cells of the flowed suspension are substantially disintegrated by the alkaline lysis solution alone to produce a lysed cell solution;

c) introducing the lysed cell solution into wherein the lysed cell solution is mixed with a neutralization solution to produce a mixture comprising a lysate and a precipitate comprising cellular debris and impurities, and wherein the lysate contains the polynucleotide of interest;

d) introducing the mixture comprising the precipitate and the lysate into the clarification reactor wherein the lysate containing the polynucleotide of interest is separated from the precipitate, wherein the mixture comprising the precipitate and the lysate is allowed to flow through the clarification reactor, and wherein the clarification reactor contains a retention layer that functions to retain the precipitate but allow the lysate to flow out of the clarification reactor; and e) purifying the polynucleotide of interest, where the polynucleotide of interest is purified from the lysate that flows out of the clarification reactor, wherein said method is operated on a manufacturing scale.

2. The method of claim 1, wherein the retention layer comprises a particulate material.

3. The method of claim 2, wherein the particulate material of the retention layer consists of glass beads.

4. The method of claim 1, wherein the retention layer comprises a rigid retention material.

5. The method of claim 4, wherein the rigid retention material comprises sinter plates.

6. The method of claim 1, wherein the clarification reactor has a top and a bottom, wherein the retention layer is disposed inside the clarification reactor between the top and the bottom of the clarification reactor, wherein the mixture comprising the precipitate and the lysate enters the top of the clarification reactor, and the lysate exits the bottom of the clarification reactor, with the precipitate being retained within the clarification reactor by the retention layer, wherein in step d), increasing pressure is applied at the top of the clarification reactor to the mixture comprising the precipitate and the lysate, thereby ensuring a constant outflow of the lysate from the bottom of the clarification reactor.

7. The method of claim 6, wherein the retention layer has a top facing the top of the clarification reactor and a bottom facing the bottom of the clarification reactor, wherein the retention layer functions to retain the precipitate on the top of and within the retention material while allowing the purified lysate to flow out of the clarification reactor.

8. The method of claim 6, wherein pressure is increased by applying pressurized gas.

9. The method of claim 8, wherein the applied pressurized gas is pressurized air.

10. The method of claim 1, wherein one or more wash steps are inserted between steps d) and e).

11. The method of claim 1, wherein the flow of the cell suspension and the flow of the lysis solution are combined, without further mixing, before entering the lysis reactor, thus forming a single flow within the lysis reactor that is homogeneously mixed when flowing through the filling elements in the lysis reactor.

12. The method of claim 11, wherein the two flows are transported through the lysis reactor at a defined ratio of flow rates, the flow rates being regulated by pressure or pumps, thereby ensuring a constant ratio of cell suspension flow volumes and lysis solution flow volumes.

13. The method of claim 1, wherein the cell suspension and the lysis solution are introduced into the lysis reactor in the form of two independent flows.

14. The method of claim 13, wherein the two flows are transported through the lysis reactor at a defined ratio of flow rates, the flow rates being regulated by pressure or pumps, thereby ensuring a constant ratio of cell suspension flow volumes and lysis solution flow volumes.

15. The method of claim 1, wherein the neutralization reactor includes a T-type or a Y-type connector and a tubing system fluidly connecting the lysis reactor to the clarification reactor, the tubing system being in the form of a coil, wherein lysed cell solution and the neutralization solution are combined through the T-type or the Y-type connector, thus forming a single flow through the tubing system, wherein the lysed cell solution and the neutralization solution are mixed to produce the mixture comprising the lysate and the precipitate during transportation through the tubing system between the lysis reactor and the clarification reactor, wherein the tubing system is configured to avoid shearing of flocks of the precipitate.

16. The method of claim 1, wherein in step c), the lysed cell solution obtained in step b) is mixed with the neutralization solution in a continuous mode.

17. The method of claim 16, wherein the lysed cell solution and the neutralization solution are combined at a constant ratio of flow rates.

18. The method of claim 1, wherein a concentration and/or a conditioning step is inserted between step d) and step e).

19. The method of claim 18, wherein the concentration step and the condition step are inserted, and wherein said concentration step takes place before said conditioning step.

20. The method of claim 1, wherein said polynucleotide of interest comprises a pDNA, a short linear DNA or RNA.

21. The method of claim 20, wherein the polynucleotide of interest is pDNA.

22. The method of claim 1 wherein step a) is operated in a continuous mode.

23. The method of claim 1, wherein the harvested cell suspension provided in step a) is cryopelleted prior to resuspension.

24. The method of claim 1, wherein one or more distribution means are disposed inside the clarification reactor and extend onto a surface of the retention layer, wherein the one or more distribution means evenly distribute the mixture comprising the precipitate and the lysate as obtained in step c) into the clarification reactor of step d).

25. The method of claim 1, wherein the filling elements are a particulate material.

26. The method of claim 25, wherein the particulate material consists of beads, each bead having a diameter in the range of about 1 to about 100 mm.

27. The method of claim 26, wherein each bead has the same diameter.

28. The method of claim 25, wherein the lysis reactor is essentially completely filled with the particulate material.

29. The method of claim 25, wherein the particulate material consists of glass beads.

30. The method of claim 1, wherein at least 100 grams wet cells are processed to provide the cell suspension and from 0.1 g to 1.0 kilogram of the polynucleotide of interest is produced, depending on the amount of wet cell paste processed and the amount of the polynucleotide of interest present in the cells.

31. The method according to claim 1, wherein said method is continuously operated on a manufacturing scale.

* * * * *

UNITED STATES PATENT AND TRADEMARK OFFICE
CERTIFICATE OF CORRECTION

| | | |
|---|---|---|
| PATENT NO. | : 8,501,402 B2 | Page 1 of 1 |
| APPLICATION NO. | : 10/806346 | |
| DATED | : August 6, 2013 | |
| INVENTOR(S) | : Jochen Urthaler et al. | |

It is certified that error appears in the above-identified patent and that said Letters Patent is hereby corrected as shown below:

In the Claims

In column 26, line 18, Claim 1 step c), please insert the term --the neutralizing reactor-- after the phrase "introducing the lysed cell solution into" and prior to the phrase "wherein the lysed cell solution is mixed.."

Signed and Sealed this
Thirty-first Day of December, 2013

Margaret A. Focarino
*Commissioner for Patents of the United States Patent and Trademark Office*

UNITED STATES PATENT AND TRADEMARK OFFICE
CERTIFICATE OF CORRECTION

| | | |
|---|---|---|
| PATENT NO. | : 8,501,402 B2 | Page 1 of 1 |
| APPLICATION NO. | : 10/806346 | |
| DATED | : August 6, 2013 | |
| INVENTOR(S) | : Urthaler et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1514 days.

Signed and Sealed this
Twenty-first Day of April, 2015

Michelle K. Lee
*Director of the United States Patent and Trademark Office*